United States Patent [19]

Petitou et al.

[11] Patent Number: 5,514,659

[45] Date of Patent: May 7, 1996

[54] 3-DEOXY OLIGOSACCHARIDES AND PHARMACEUTICAL COMPOSITIONS CONTAINING THEM

[75] Inventors: Maurice Petitou, Paris; Guy F. B. Jaurand, Chateaufort, both of France; Constant A. A. Van Boeckel, Lx Oss, Netherlands

[73] Assignees: Elf Sanofi, Paris, France; Akzo Nobel NV, BM Arnheim, Netherlands

[21] Appl. No.: 230,921

[22] Filed: Apr. 21, 1994

[30] Foreign Application Priority Data

Apr. 22, 1993 [FR] France ................................. 93 04769

[51] Int. Cl.$^6$ ................................................ A61K 31/725
[52] U.S. Cl. ...................... 514/25; 514/54; 514/56; 536/4.1; 536/21; 536/118; 536/119; 536/122; 536/123.1
[58] Field of Search ................................ 514/25, 54, 56; 536/4.1, 21, 118, 119, 122, 123.1

[56] References Cited

U.S. PATENT DOCUMENTS

| | | | |
|---|---|---|---|
| 4,788,307 | 11/1988 | Lormeau et al. | 536/21 |
| 4,804,652 | 2/1989 | Lormeau et al. | 514/56 |
| 4,818,816 | 4/1989 | Petitou et al. | 536/55.2 |
| 4,826,827 | 5/1989 | Lormeau et al. | 514/56 |
| 4,990,502 | 2/1991 | Lormeau et al. | 514/56 |

FOREIGN PATENT DOCUMENTS

| | | |
|---|---|---|
| 0454220 | 4/1990 | European Pat. Off. . |
| 0529715 | 3/1993 | European Pat. Off. . |

OTHER PUBLICATIONS

Zuurmond et al. *J. Carbohydr. Chem.* 1993, 12(8), 1091–1103.

Hirasaka et al. *Chem. Pharm. Bull.* 1965, 13(6), 672–676.

Kreuzer et al. *Carbohydr. Res.* 1986, 149(2), 347–361.

H. Lucas et al., "A short synthetic route towards a biologically active heparin-like penta-saccharide with a pseudo-alternating sequence", Angewandte Chemie International Edition In English, vol. 32, No. 3, Mar. 1993, Weinheim, Germany, pp. 434–436.

*Primary Examiner*—Douglas W. Robinson
*Assistant Examiner*—Kathleen Kahler Fonda
*Attorney, Agent, or Firm*—Jacobson, Price, Holman & Stern

[57] ABSTRACT

The invention relates to 3-deoxy oligosaccharides of formula I:

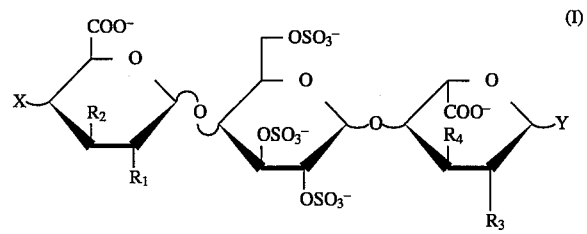

in which

X represents an $-OSO_3^-$ radical, a radical of formula R—O, a radical of formula:

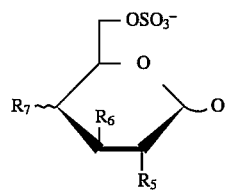

or a radical of formula:

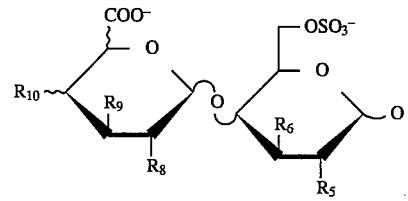

Y represents a radical of formula:

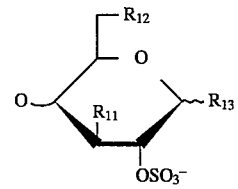

R represents an alkyl radical, $R_1$, $R_3$, $R_5$, $R_7$, $R_8$, $R_{10}$, $R_{12}$ and $R_{13}$ represent a hydroxyl radical, an alkoxy radical or an $-OSO_3^-$ radical, $R_2$, $R_4$, $R_6$, $R_9$ and $R_{11}$ represent a hydrogen atom, a hydroxyl radical, an alkoxy radical or an $-OSO_3^-$ radical, with the proviso that at least $R_2$ or $R_4$ or $R_6$ or $R_9$ or $R_{11}$ represents a hydrogen atom, and their pharmaceutically acceptable salts with a base.

13 Claims, No Drawings

3-DEOXY OLIGOSACCHARIDES AND PHARMACEUTICAL COMPOSITIONS CONTAINING THEM

The present invention relates to 3-deoxy oligosaccharides, to processes for preparing them and to pharmaceutical compositions containing them.

Heparin is a polysaccharide of the glycosaminoglycan family which is known for its anticoagulant properties. It is known (I. Björk and U. Lindahl, "Molecular and Cellular Biochemistry", (1982), Dr. W. Junk Publishers—Holland) that blood coagulation is a complex physiological phenomenon. Certain stimuli, such as contact activation and tissue factors, trigger the successive activation of a series of coagulation factors present in blood plasma. Irrespective of the nature of the stimulus, the final steps are identical: activated factor X (Xa) activates factor II (also known as pro-thrombin) which, in its activated form (factor IIa, also known as thrombin), causes the partial proteolysis of soluble fibrinogen with release of insoluble fibrin, the main constituent of the blood clot.

Under normal physiological conditions, the activity of the coagulation factors is regulated by proteins such as antithrombin III (AT III) and heparin cofactor II (HC II), which are also present in plasma. AT III exerts an inhibitory activity on a number of coagulation factors, and in particular on factors Xa and IIa.

The inhibition of factor Xa or of factor IIa hence constitutes a favored means for obtaining anticoagulant and antithrombotic activity, since these two factors participate in the last two steps of coagulation, which are independent of the triggering stimulus.

The pentasaccharide of formula:

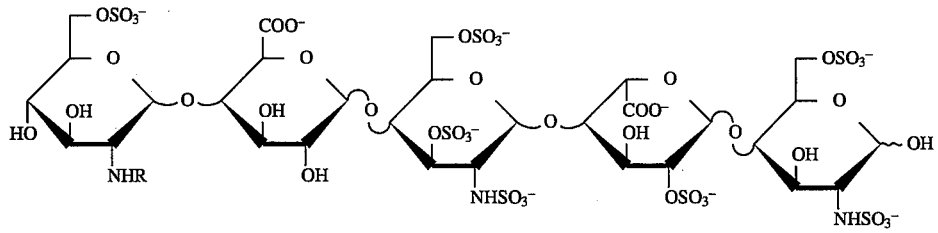

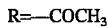        (1)

        (2)

represents the minimum sequence of heparin required for binding the AT III. This compound (R=—SO$_3^-$) was obtained approximately ten years ago by total chemical synthesis (P. Sinaÿ et al, Carbohydrate Research (1984), 132 C5).

Since then, a number of synthetic oligosaccharides obtained by total chemical synthesis and having antithrombotic and anticoagulant activities have been described in the literature.

Patent EP-0,084,999 describes derivatives consisting of uronic (glucuronic or iduronic) acid and glucosamine monosaccharide units and possessing advantageous antithrombotic properties. Besides the hydroxyl group substituents, these compounds contain N-sulphate groups and N-acetyl groups and, in some cases, the anomeric hydroxyl groups are replaced by methoxy groups.

Application EP-0,165,134 also describes synthetic oligosaccharides having antithrombotic activity. These compounds consist of uronic acid and glucosamine monosaccharide units and contain O-sulphate or O-phosphate groups. Derivatives of uronic acids and of glucosamine containing an O-sulphate group at position 3 of the glucosamine unit are also described in Application EP-0,301,618. These compounds possess enhanced antithrombotic and anticoagulant properties. Patent Application EP-0,454,220 describes derivatives of uronic acids and of glucose possessing O-alkyl or O-sulphate groups as substituents. These latter compounds are also endowed with antithrombotic and anticoagulant properties.

Sulphated glycosaminoglycanoid derivatives in which the N-sulphate, N-acetate or hydroxyl functional groups have been replaced by alkoxy, aryloxy, aralkyloxy or O-sulphate groups are also described in Application EP-0,529,715. These compounds have advantageous antithrombotic properties. They are also inhibitors of the proliferation of smooth muscle cells.

Oligosaccharides, and in particular pentasaccharides, which are analogues of the minimum sequence of heparin required for binding to AT III are described in Agnew. Chem. Int. Ed. Engl. (1993), 32, (3), pp. 434–436. These compounds contain glucuronic acid or glucose units in which the hydroxyl groups have been replaced by O-sulphate or O-methyl groups.

It has now been found that, surprisingly, by replacing one or more hydroxyl radicals or O-alkyl or O-sulphate groups at position 3 by hydrogen atoms, on one or more saccharide units, oligosaccharides endowed with advantageous biological properties are obtained. In effect, the compounds of the present invention differ from the other synthetic heparinoids described in the literature by their novel structures and by their potent and unexpected biological properties. The compounds of the invention are 3-deoxy oligosaccharides possessing very great anti-factor Xa activity and great affinity for AT III. Moreover, the compounds of the invention are well absorbed via the digestive tract. Hence they are products which can be administered orally.

The subject of the present invention is, more especially, the compounds of formula I:

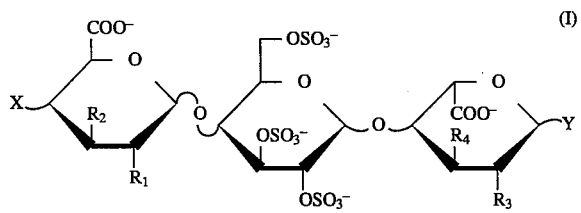

in which

X represents an —OSO$_3^-$ radical, a radical of formula A,

R—O        (A)

a radical of formula B,

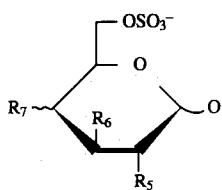
(B)

or a radical of formula C,

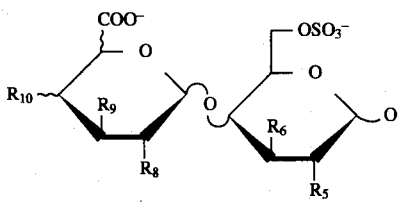
(C)

Y represents a radical of formula D,

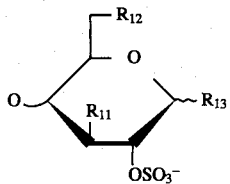
(D)

Hereinafter, the term "monosaccharide unit" will be used to denote the glycoside unit:

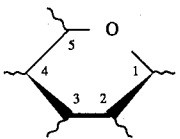

independently of the substituents which will be linked to this unit as positions 2, 3 or 5.

As regards the radicals B, C and D, the bond ⌇means that, in some cases, the configuration of the carbon bearing the substituent attached via this bond can be R, and in other cases S.

The compounds of the present invention are 3-deoxy saccharide derivatives.

Hence at least one of the monosaccharide units from which the compounds of the invention are formed must correspond to the structure of a 3-deoxy monosaccharide.

As a result, in the formula I, at least one of the substituents $R_2$ or $R_4$ or $R_6$ or $R_9$ or $R_{11}$ represents a hydrogen atom.

The compounds of formula I in which $R_2$ represents a hydrogen atom are preferred products of the invention.

Preferred compounds of the present invention are also the compounds of formula I in which X represents a radical of formula (B) or a radical of formula (C).

These compounds correspond to the following formulae Ia and Ib:

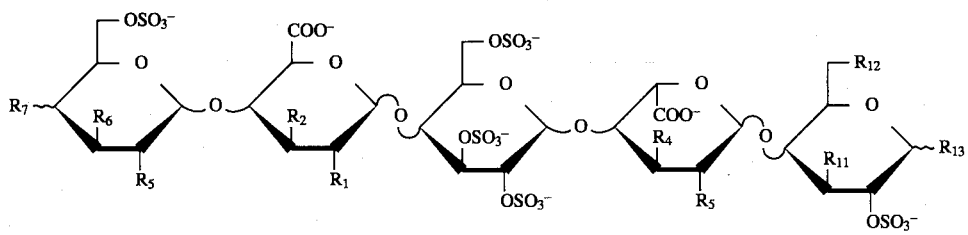
(Ia)

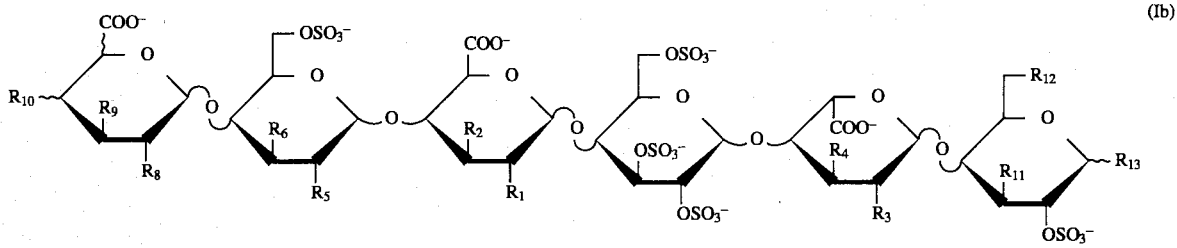
(Ib)

R represents a linear or branched alkyl radical having 1 to 6 carbon atoms, $R_1$, $R_3$, $R_5$, $R_7$, $R_8$, $R_{10}$, $R_{12}$ and $R_{13}$, which may be identical or different, each represent a hydroxyl radical, a linear or branched alkoxy radical having 1 to 6 carbon atoms or an —$OSO_3^-$ radical, $R_2$, $R_4$, $R_6$, $R_9$ and $R_{11}$, which may be identical or different, each represent a hydrogen atom, a hydroxyl radical, a linear or branched alkoxy radical having 1 to 6 carbon atoms or an —$OSO_3^-$ radical, with the proviso that at least one of the substituents present, $R_2$ or $R_4$ or $R_6$ or $R_9$ or $R_{11}$, represents a hydrogen atom, in the form of pharmaceutically acceptable salts and the corresponding acids.

in which $R_1$, $R_2$, $R_3$, $R_4$, $R_5$, $R_6$, $R_7$, $R_8$, $R_9$, $R_{10}$, $R_{11}$, $R_{12}$ and $R_{13}$ have the same meaning as for the formula I.

The compounds of formula Ia are more especially preferred.

The compounds of formula I, and more especially those of formula Ia and Ib, in which:

$R_1$, $R_3$, $R_5$, $R_7$, $R_8$, $R_{10}$ and $R_{13}$, which may be identical or different, each represent a linear or branched alkoxy radical having 1 to 6 carbon atoms or an —$OSO_3^-$ radical, $R_2$, $R_4$, $R_6$ and $R_9$, which may be identical or different, each represent a hydrogen atom or a linear or branched alkoxy radical having 1 to 6 carbon atoms, $R_{11}$ represents a hydrogen atom, a linear or branched alkoxy radical having 1 to 6 carbon atoms or an —$OSO_3^-$ radical.

With the proviso that at least $R_2$ or $R_4$ or $R_6$ or $R_9$ or $R_{11}$ represents a hydrogen atom, and $R_{12}$ represents a hydroxyl radical or an —$OSO_3^-$ radical, are preferred compounds of the invention.

Preference is given more especially to the compounds of formula I, and in particular those of formulae Ia and Ib, in which:

$R_2$ and $R_6$ represent a hydrogen atom, $R_3$, $R_{11}$ and $R_{12}$ represent an —$OSO_3^-$ radical, and $R_{13}$ represents a linear or branched alkoxy radical having 1 to 6 carbon atoms.

Preference is also given more especially to the compounds of formula I, and in particular those of formulae Ia and Ib, in which the alkoxy radical is a methoxy radical.

The subject of the present invention is also a process for preparing the compounds of formula I, characterized in that a compound of formula II:

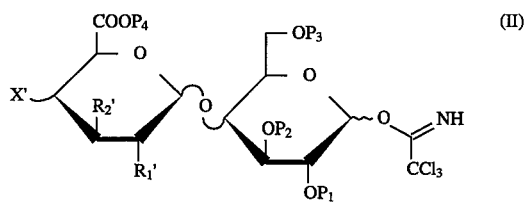

in which

X' represents a chloroacetoxy radical, a laevulinyloxy radical, a radical of formula A, a radical of formula $B_1$,

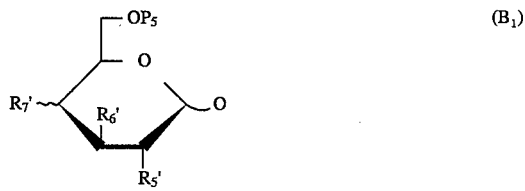

or a radical of formula $C_1$,

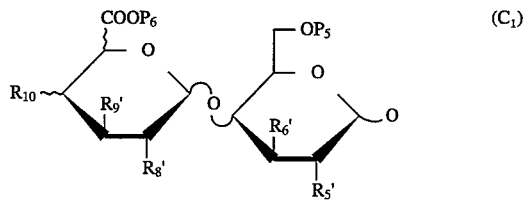

$P_1$, $P_2$, $P_3$ and $P_5$, which may be identical or different, each represent a protective group such as an acyclic acyl radical having 1 to 6 carbon atoms, preferably an acetyl radical, an aromatic acyl radical, preferably a benzoyl radical, a 2-alkenyl radical having 2 to 7 carbon atoms, preferably an allyl radical, or a benzyl radical, $P_4$ and $P_6$, which may be identical or different, each represent a protective group such as an alkyl radical having 1 to 6 carbon atoms, preferably a methyl radical, or a benzyl radical, $R_1'$, $R_5'$ and $R_8'$, which may be identical or different, each represent a linear or branched alkoxy radical having 1 to 6 carbon atoms, an acyclic acyloxy radical having 1 to 6 carbon atoms, preferably an acetoxy radical, an aromatic acyloxy radical, preferably a benzoyloxy radical, or a 2-alkenyloxy radical having 2 to 7 carbon atoms, preferably an allyloxy radical, $R_7'$ and $R_{10}'$, which may be identical or different, have the meanings given for $R_1'$, or they represent a chloroacetoxy radical or a laevulinyloxy radical, and $R_2'$, $R_6'$ and $R_9'$, which may be identical or different, each represent a hydrogen atom or have the meanings given for $R_1'$, is reacted with a compound of formula III:

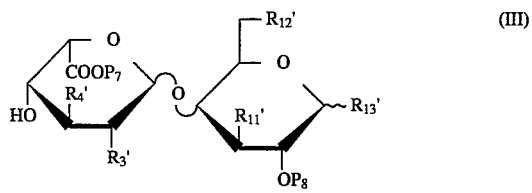

in which $P_7$ has the meanings given for $P_4$ in the formula II, $P_8$ has the meanings given for $P_1$ in the formula II, $R_4'$ and $R_{11}'$, which may be identical or different, have the same meanings as $R_2'$ in the formula II, and $R_3'$, $R_{12}'$ and $R_{13}'$, which may be identical or different, have the meanings given for $R_1'$ in the formula II, to prepare the compounds of formula IV:

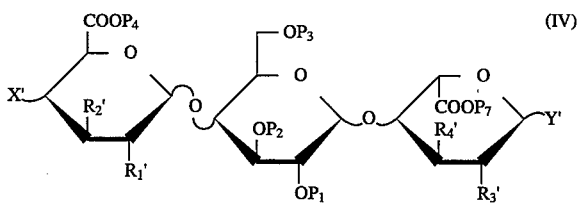

in which

X', $P_1$, $P_2$, $P_3$, $P_4$, $R_1'$ and $R_2'$ have the same meaning as for the formula II, $P_7$, $R_3'$ and $R_4'$ have the same meaning as for the formula III, and Y' represents a radical of formula $D_1$:

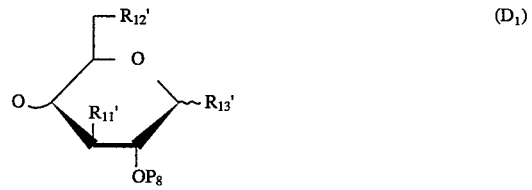

in which $P_8$, $R_{11}'$, $R_{12}'$ and $R_{13}'$ have the same meaning as for the formula III, which is thereafter subjected either to a catalytic hydrogenation, then to a saponification and to a sulphation, or first to a saponification, then to a sulphation and thereafter to a catalytic hydrogenation, or first to a catalytic hydrogenation, then to a sulphation and thereafter to a saponification, to obtain the compounds of formula I.

The process described above is the preferred process of the invention. However, the compounds of formula I may be prepared by other known methods of sugar chemistry, and in particular by reacting a monosaccharide containing protective groups, such as are described by T. W. Green, in Protective Groups in Organic Synthesis (Wiley, N.Y. 1981), on the hydroxyl radicals and, where appropriate, on the carboxyl radicals if it has any, with another protected monosaccharide, to form a disaccharide which is thereafter reacted with another protected monosaccharide, to form a protected trisaccharide from which it is possible to obtain a protected tetrasaccharide, then a protected pentasaccharide and thereafter a protected hexasaccharide ("stepwise" approach).

The protected oligosaccharides (tetra-, penta- and hexasaccharide) are thereafter deprotected and, where appropriate, sulphated, or first partially deprotected, then sulphated and thereafter deprotected, to obtain compounds of formula I.

Such processes are known in carbohydrate chemistry, and are described, especially by G. Jaurand et al. in Bioorganic and Medicinal Chemistry Letters (1992), 2 (No. 9), pp. 897–900, by J. Basten et al. in Bioorganic and Medicinal Chemistry Letters (1992), 2 (No. 9), pp. 901–904, by J. Basten et al. in Bioorganic and Medicinal Chemistry Letters (1992), 2 (No. 9), pp. 905–910 and by M. Petitou and C. A. A. van Boeckel in "Chemical Synthesis of heparin fragments and analogues" pp. 203–210—Progress in the Chemistry of Organic Natural Products, Ed. Springer Verlag Vienna—N.Y. (1992).

The compounds of formula II, when X' represents a radical of formula $B_1$, may be prepared by reacting a monosaccharide which is activated on its anomeric carbon, such as, for example, a compound of formula V:

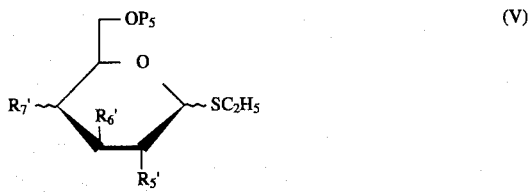

in which $P_5$, $R_5'$, $R_6'$ and $R_7'$ have the same meaning as for the formula $B_1$, with a compound of formula VI:

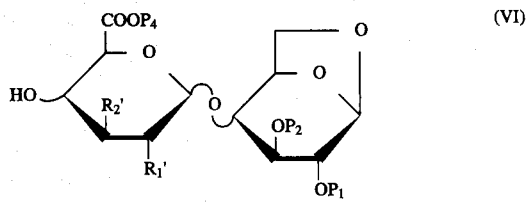

in which $R_1'$, $R_2'$, $P_1$, $P_2$ and $P_4$ have the same meaning as for the formula II, to obtain thereby a compound of formula VII:

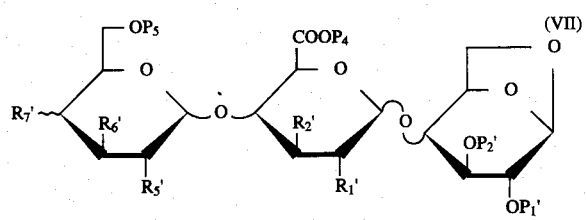

in which $P_5$, $R_5'$, $R_6'$ and $R_7'$ have the same meaning as for the formula V, and $R_1'$, $R_2'$, $P_1$, $P_2$ and $P_4$ above the meaning given for the formula II, according to the process described by T. Peters et al. in Can. J. Chem., (1989), 67, pp. 491–496 and by G. H. Veeneman and J. H. van Boom in Tetrahedron Letters (1990), 31, pp. 275–278.

By treating this compound according to known processes (R. Schmidt, Agnew. Chem. Int. Ed, England (1986), 25, (3), pp. 212–235), and in particular by acetolysis, treatment with benzylamine and then with trichloroacetonitrile, the compounds of formula II in which X' represents a radical of formula $B_1$ are obtained.

The preparation of some compounds of formula VII, and in particular the compounds for which $R_2'$ and $R_6'$ have the meanings given for $R_1'$ and do not represent a hydrogen atom is described by J. Basten et al. (Bioorganic and Medicinal Chemistry Letters (1992), 2 (No. 9), pp. 905–910).

The compounds of formula VII may also be prepared by reacting the compounds VI with other activated monosaccharides, for example with the compounds of formula V':

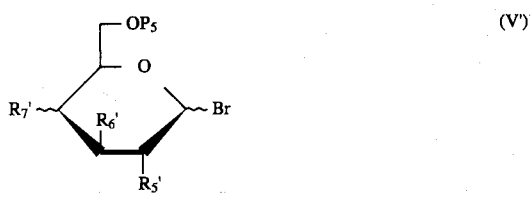

in which $P_5$, $R_5'$, $R_6'$ and $R_7'$ have the same meaning as for the formula V.

The compounds of formula V' for which $R_6'$ has the meanings given for $R_1'$ and does not represent a hydrogen atom are known compounds which are described by M. Petitou and C. A. A. van Boeckel in "Chemical Synthesis of heparin fragments and analogues" pp. 203–210—Progress in the Chemistry of Organic Natural Products, Ed. Springer Verlag Vienna—N.Y. (1992).

Compounds of formula V in which $R_6'$ represents a hydrogen atom may be obtained from a compound of formula VIII:

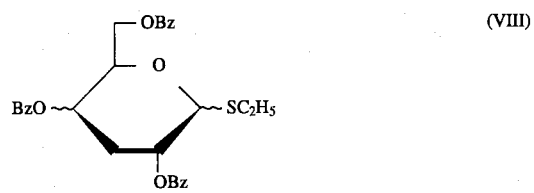

in which Bz represents a benzoyl radical.

The compound of formula VIII is prepared from 3-deoxy-β-D-ribo-hexopyranose (prepared according to the method of T. V. Rajanbabu, described in J. Org. Chem., (1988), 53, pp. 4522–4530), which is subjected to the action of benzoyl chloride in a basic organic solvent. The compound thereby obtained is subjected to the action of ethanethiol to obtain the compounds of formula VIII.

The compounds of formula VI, when $R_2'$ represents a hydrogen atom, may also be obtained from the compound of formula VIII, which is reacted with 1,6:2,3-dianhydro-β-D-mannopyranose, to obtain a compound of formula IX:

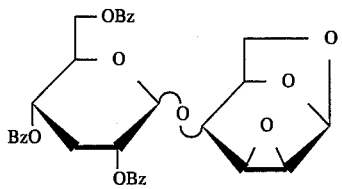
(IX)

in which Bz represents a benzoyl radical.

This compound is then subjected to the action of a strong base to obtain 1,6:2,3-dianhydro-4-O-(3-deoxy-β-D-ribo-hexopyranosyl)-β-D-mannopyranose, the compound of formula X:

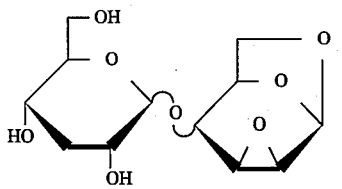
(X)

From the compound of formula X, and using standard methods [G. Jaurand et al., Bioorganic and Medicinal Chemistry Letters (1992), 2 (No. 9), pp. 897–900; J. Basten et al., Bioorganic and Medicinal Chemistry Letters (1992), 2 (No. 9), pp. 901–904; J. Basten et al., Bioorganic and Medicinal Chemistry Letters (1992), 2 (No. 9), pp. 905–910; M. Petitou and C. A. A. van Boeckel "Chemical Synthesis of heparin fragments and analogues" pp. 203–210—Progress in the Chemistry of Organic Natural Products, Ed. Springer Verlag Vienna—N.Y. (1992)], the compounds of formula XI:

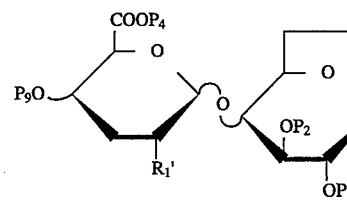
(XI)

in which $R_1'$, $P_1$, $P_2$ and $P_4$ have the same meaning as for the formula VII, and $P_9$ represents a laevulinyl radical or a chloroacetyl radical, are obtained.

The compound of formula XI is then subjected to the action of hydrazine to obtain the compounds of formula VI in which $R_2'$ represents a hydrogen atom.

The compounds of formula IX, X and XI are new products and also form part of the invention.

The compounds of formula VI for which $R_2'$ has the meanings given for $R_1'$ and which does not represent a hydrogen atom may be obtained in a similar manner, using as starting materials protected glucose derivatives which are activated on their anomeric carbon instead of the compounds of formula VIII. The preparation of such compounds is described by M. Petitou and C. A. A. van Boeckel in "Chemical Synthesis of heparin fragments and analogues" pp. 203–210—Progress in the Chemistry of Organic Natural Products, Ed. Springer Verlag Vienna—N.Y. (1992). The same authors also describe the analogous preparation of the compounds of formula IX containing a protected hydroxyl radical at position 3.

The compounds of formula II, when X' represents a radical of formula $C_{1a}$:

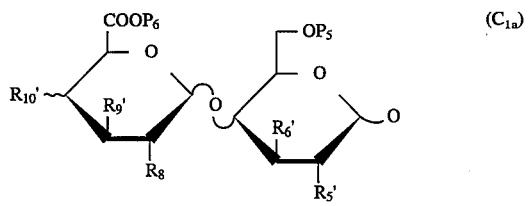
($C_{1a}$)

in which $R_5'$, $R_6'$, $R_8'$, $R_9'$, $R_{10}'$, $P_5$ and $P_6$ have the same meaning as for the formula $C_1$, may be obtained by reacting a compound of formula VI with a compound of formula XIIa:

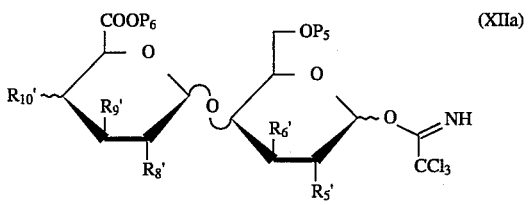
(XIIa)

in which $R_5'$, $R_6'$, $R_8'$, $R_9'$, $R_{10}'$, $P_5$ and $P_6$ have the same meaning as for the formula $C_1$, to obtain a compound of formula XIIIa:

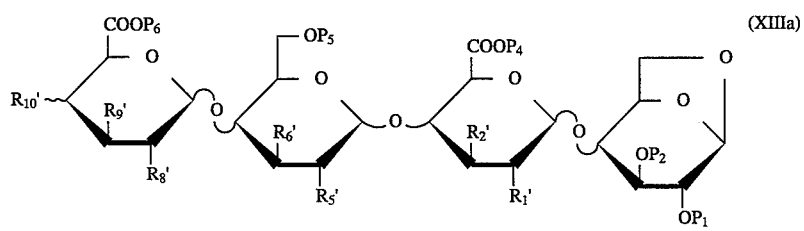
(XIIIa)

in which $R_5'$, $R_6'$, $R_8'$, $R_9'$, $R_{10}'$, $P_5$ and $P_6$ have the same meaning as for the formula $C_1$, and $R_1'$, $R_2'$, $P_1$, $P_2$ and $P_4$ have the meanings given for the formula II.

The compounds of formula XIIIa are then treated as indicated for the compound VII, to obtain the compounds of formula II in which X' represents a radical of formula $C_{1a}$.

The compounds of formula XIIa, when $R_9'$ represents a hydrogen atom, are obtained from the compounds of formula XIV:

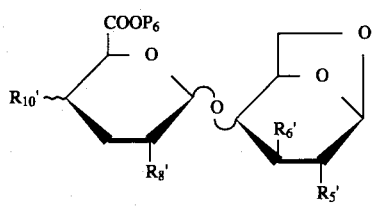

in which $R_5'$, $R_6'$, $R_8'$, $R_{10}'$ and $P_6$ have the same meaning as for the formula $C_1$, which is subjected to an acetolysis, to a deprotection and then to the action of trichloroacetronitrile. The compounds of formula XIV may be obtained from the compounds of formula X according to the process described for the compounds of formula XI.

The compounds of formula XIIa, when $R_9'$ has the meanings given for $R_1'$ and does not represent a hydrogen atom, are prepared from 1,6:2,3-dianhydro-4-O-(β-D-glycopyranosyl)-β-D-mannopyranose derivatives by applying the process described above. 1,6:2,3-Dianhydro-4-O-(β-D-glucopyranosyl)-β-D-mannopyranose derivatives are known products described by J. Basten et al. in Bioorganic and Medicinal Chemistry Letters (1992), 2 (No. 9), pp. 905–910.

The compounds of formula II, when X' represents a radical of formula $C_{1b}$:

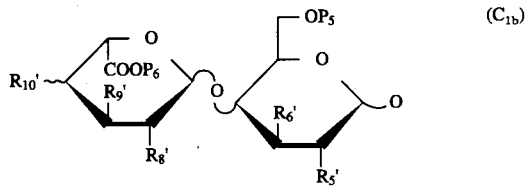

in which $R_5'$, $R_6'$, $R_8'$, $R_9'$, $R_{10}'$, $P_5$ and $P_6$ have the same meaning as for the formula $C_1$, may be obtained by reacting a compound of formula XIIb:

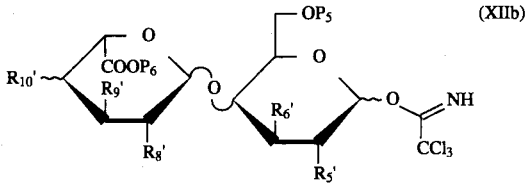

in which $R_5'$, $R_6'$, $R_8'$, $R_9'$, $R_{10}'$, $P_5$ and $P_6$ have the meanings given for the formula $C_1$, with a compound of formula VI, to obtain the compounds of formula XIIIb:

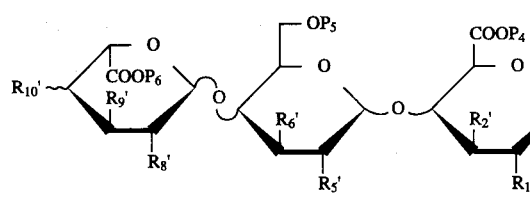

in which $R_1'$, $R_2'$, $R_5'$, $R_6'$, $R_8'$, $R_9'$, $R_{10}'$, $P_1$, $P_2$, $P_4$, $P_5$ and $P_6$ have the same meanings as for the formula XIIIa.

The compounds of formula XIIIb are then treated as indicated for the compounds of formula XIIIa, to obtain the compounds of formula II in which X' represents a radical of formula $C_{1b}$.

The compounds of formula XIIb, when $R_9'$ represents a hydrogen atom, may be obtained from the compounds of formula X. This compound is converted to a compound of formula XV:

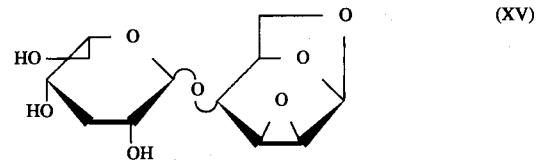

according to a process equivalent to that described by Ichikawa et al. in Carbohydrate Research, (1988), 172, pp. 37–64.

From this compound, and using known methods described by G. Jaurand et al. in Bioorganic and Medicinal Chemistry Letters (1992), 2 (No. 9), pp. 897–900, by J. Basten et al. in Bioorganic and Medicinal Chemistry Letters (1992), 2 (No. 9), pp. 901–904, by J. Basten et al. in Bioorganic and Medicinal Chemistry Letters (1992), 2 (No. 9), pp. 905–910 and M. Petitou and C. A. A. van Boeckel "Chemical Synthesis of heparin fragments and analogues" pp. 203–210—Progress in the Chemistry of Organic Natural Products, Ed. Springer Verlag Vienna—N.Y. (1992), the compounds of formula XVI:

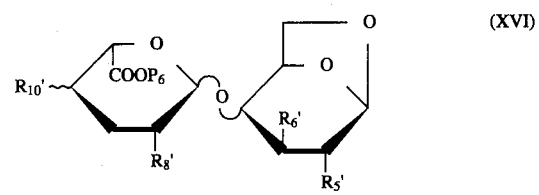

in which $R_5'$, $R_6'$, $R_8'$, $R_{10}'$ and $P_6$ have the same meaning as for the formula XIIb, are obtained.

These compounds are thereafter subjected to an acetolysis and then treated with benzylamine and trichloroacetronitrile to obtain the compounds of formula XIIb.

The compounds of formula XIIb for which $R_9'$ does not represent a hydrogen atom but has the meanings given for $R_1'$ may be obtained in the same manner.

The various intermediates that make it possible to obtain the compounds of formula XIIb in which $R_5'$, $R_6'$, $R_8'$, $R_{10}'$, $P_5$ and $P_6$ have the same meaning as for the formula $C_1$, and $R_9'$ has the meanings given for $R_1'$ and does not represent a hydrogen atom, are known products, and their preparation is described by G. Jaurand et al. in Bioorganic and Medicinal Chemistry Letters (1992), 2 (No. 9), pp. 897–900.

The compounds of formula II, when X' represents a radical of formula A and $R_2'$ represents a hydrogen atom, may be obtained from the compound of formula X, which is converted to a compound of formula XVII:

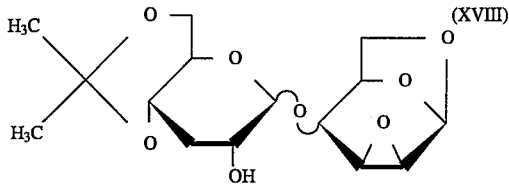

The compound of formula XVII is next either treated with sodium benzylate and then acylated, or treated with an aralkyl halide, preferably benzyl bromide, or a 2-alkenyl halide, preferably allyl bromide, then treated with sodium benzylate and thereafter acylated, to obtain the compounds of formula XVIII:

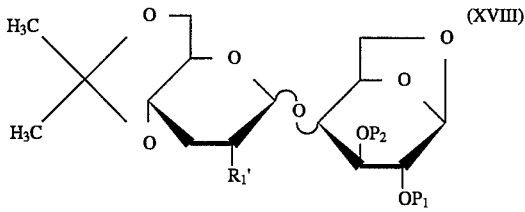

in which $R_1'$, $P_1$ and $P_2$ have the same meaning as for the formula II.

The compounds of formula XVIII are then treated in an acid medium to obtain the compounds of formula XIX:

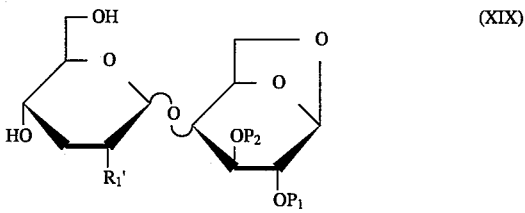

in which $R_1'$, $P_1$ and $P_2$ have the meanings given for the formula II.

The compounds of formula XIX are then subjected to a selective silylation at position 6', treated with laevulinic anhydride, oxidized according to Jones' conditions and esterified using an alkyl halide, subjected to removal of the laevulinyl radical and alkylated in an acid or neutral medium, to obtain the compounds of formula II in which X' represents a radical of formula A and $R_2'$ represents a hydrogen atom.

In the same manner, the compounds of formula II, when X' represents a radical of formula A and $R_2'$ has the meanings given for $R_1'$, may be obtained. The intermediates needed for the preparation of these compounds are described in the literature, and in particular by J. Basten et al., in Bioorganic and Medicinal Chemistry Letters (1992), 2 (No. 9), pp. 905–910, and by C. A. A. van Boeckel et al. in J. Carbohydrate Chem. (1985), 4, p. 293.

The compounds of formula III, when $R_4'$ represents a hydrogen atom, may be prepared from the compounds of formula XX:

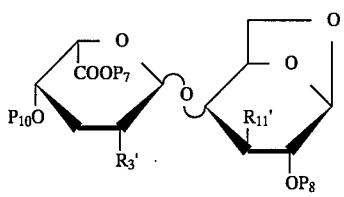

in which
$R_3'$, $R_{11}'$, $P_7$ and $P_8$ have the meanings given for the formula III, and
$P_{10}$ represents a laevulinyl radical or a chloroacetyl radical.

The compounds of formula XX are subjected to an acetolysis, then treated with benzylamine, reacted with Vilsmeier's reagent, treated with an alcohol in the presence of silver carbonate and thereafter subjected to the action of hydrazine, to obtain the expected compounds of formula III ($R_4'$=H).

The compounds of formula III, when $R_4'$ has the same meanings as $R_1'$, are known compounds. The preparation of such compounds is described in the literature by J. Basten et al. in Bioorganic and Medicinal Chemistry Letters (1992), 2 (No. 9), pp. 905–910.

The process described above enables the compounds of the invention to be obtained in the form of salts. To obtain the corresponding acids, the compounds of the invention in the form of salts are brought into contact with a cation exchange resin in acid form.

The compounds of the invention in the form of acids may then be neutralized with a base to obtain a desired salt.

For the preparation of the salts of the compounds of formula I, any inorganic or organic base giving pharmaceutically acceptable salts with the compounds of formula I may be used.

It is preferable to use sodium, potassium, calcium or magnesium hydroxide. The sodium and calcium salts of the compounds of formula I are the preferred salts.

The compounds of formula I which are the subject of the present invention have advantageous pharmacological and biochemical properties. They possess, more especially, great anti-factor Xa activity and great affinity for AT III.

As mentioned above, in the coagulation cascade, factor Xa activates prothrombin to thrombin, which causes proteolysis of the soluble fibrinogen with release of insoluble fibrin, the main constituent of the blood clot. The inhibition of factor Xa hence constitutes a favoured means for obtaining anticoagulant and antithrombotic activity.

The anti-factor Xa (anti-Xa) activity of the products of the invention was evaluated at pH 8.4 according to the method described by Teien A. N. and Lie M. in Thrombosis Research (1977), 10, pp. 339–410, and it was demonstrated that the products of the invention possess an anti-Xa activity equal to or greater than that of the already known synthetic heparinoids.

The affinity of the compounds of formula I for AT III was determined by spectrofluorometry under the conditions described by D. Atha et al. in Biochemistry (1987), 26, pp. 6454–6461. The results of the tests showed that the compounds of the invention possess very great affinity for AT III.

Moreover, the overall antithrombotic activity of the products of formula I was evaluated in rats by a model of venous stasis and induction with thromboplastin, according to the method described by J. Reyers et al. in Thrombosis Research (1980), 18, pp. 669–674. The $ED_{50}$ of the compounds of the invention is at least of the same order as, or less than, that of the other, already known synthetic heparinoids. The compounds of the invention hence display an especially advantageous specificity of action and anticoagulant and antithrombotic activity.

The results obtained in various pharmacokinetic studies performed with the products of the invention demonstrated that they are very well absorbed and that their half-life is long. This makes it possible to envisage the possibility of a single daily administration when they are used in therapy.

These studies also demonstrated that the products of formula I which are the subject to the present invention are absorbed via the digestive tract, without the quantities administered being prohibitive for use in human therapy. The compounds of the invention are hence useful for the preparation of pharamceutical compositions which can be administered both parenterally and orally.

The compounds of formula I have very low toxicity; their toxicity is entirely compatible with their use as medicinal products.

The compounds of the invention can also find application in the treatment of proliferation of smooth muscle cells, since it has been demonstrated that they exert an inhibitory effect which is substantially greater than that of heparin on the growth of smooth muscle cells.

The compounds of the invention are also active on angiogenesis and are useful for the treatment of some infections caused by retroviruses.

Moreover, the compounds of the invention also exert a protective and regenerative action on nerve fibres.

The compounds of the invention are very stable, and accordingly they are especially suitable for forming the active ingredient of medicinal products.

The invention also extends to pharmaceutical compositions containing as active ingredient a compound of formula I or one of its pharmaceutically acceptable salts, optionally in combination with one or more inert and suitable excipients.

The pharmaceutical compositions thereby obtained are advantageously presented in various forms, such as, for example, solutions to be injected or swallowed, dragées, tablets or hard gelatin capsules. Injectable solutions are the preferred pharmaceutical dosage forms.

The pharmaceutical compositions containing as active ingredient at least one compound of formula I or one of its salts are, in particular, useful for the preventive or curative treatment of disorders of the vascular wall such as atherosclerosis and arteriosclerosis, and the hypercoagulability states observed, for example, following surgical operations, development of tumours or disturbances of coagulation induced by bacterial, viral or enzymatic activators.

The dosage can vary widely in accordance with the patient's age, weight and state of health, the nature and severity of the complaint and also the administration route. This dosage comprises the administration of one or several doses of approximately 0.5 mg to 1000 mg daily, preferably approximately 1 to 100 mg daily, for example about 20 mg daily, intramuscularly or subcutaneously, in discontinuous administrations or at regular intervals, or of a daily dose of about 200 mg to 1000 mg via the oral route.

These doses may naturally be adjusted for each patient in accordance with the observed results and the blood analyses performed beforehand. Subcutaneous administration is the preferred route.

The invention is illustrated by the examples below.

PREPARATIONS

Preparation I

Ethyl 2,4,6-tri-O-benzoyl-3-deoxy-1-thio-D-ribo-hexopyranoside (Compound of formula VIII)

Stage A 1,2,4,6-Tetra-O-benzoyl-3-deoxy-β-D-ribo-hexopyranose

Heat at 60° C. for 4 hours 66 mmol of 3-deoxy-1,2:5,6-di-O-isopropylidene-D-ribo-hexofuranose (T. V. Rajanbabu, J. Org. Chem. (1988), 53, pp. 4522–4530) dissolved in a mixture of water and ethanol and in the presence of a Dowex acid resin, to obtain 3-deoxy-D-ribo-hexopyranose. Evaporate to dryness, then dry by evaporating in the presence of pyridine.

Dissolve the syrup thereby obtained in 150 ml of pyridine and add 356 mmol of benzoyl chloride. Leave stirring at room temperature for 3 hours. Evaporate to dryness, dilute in dichloromethane, wash with water and crystallize in ethyl acetate to obtain 7.66 g of 1,2,4,6-tetra-O-benzoyl-3-deoxy-β-D-ribo-hexopyranose.

Yield: 30%

Melting point: 164° C.

$[\alpha]_D^{20} = +1°$ (C=1.33 in $CH_2Cl_2$)

Stage B

Dissolve 4.51 mmol of the compound obtained in the preceding stage in anhydrous toluene and under an argon atmosphere at 20° C., then add 9.03 mmol of ethanethiol.

Add 4.51 mmol of boron trifluoride dissolved in ethyl ether and leave stirring for 3 hours. Evaporate to dryness after washing with water, and purify the residue obtained in the form of a syrup on a silica column. 1.64 g of a mixture of α and β anomers of ethyl 2,4,6-tri-O-benzoyl-3-deoxy-1-thio-D-ribo-hexopyranoside are thereby obtained.

This compound is used without further purification.

Yield: 70%

Preparation II

Ethyl 2,4,6-tri-O-benzyl-3-deoxy-1-thio-D-ribo-hexopyranoside (Compound of formula V)

Dissolve 5.82 mmol of the compound obtained in Preparation I in a mixture of methanol and dichloromethane (1:1 V/V). Add 0.90 mmol of sodium methanolate. Leave the reaction mixture stirring for 3 hours at 20° C., then neutralize using a Dowex acid resin (AG 50 WX2). Filter and evaporate to dryness. Dissolve the residue in 18 ml of anhydrous dimethylformamide, then add at 0° C. 19.7 mmol of sodium hydride and 17.0 mmol of benzoyl bromide. Leave stirring for 2 hours, then add 34.1 mmol of methanol.

Evaporate the reaction solvents and purify on a silica column, to obtain 2.12 g of the expected product in the form of a mixture of anomers.

Yield: 76%

Preparation III 1,6:2,3-Dianhydro-4-O-(2,4,6-tri-O-benzoyl-3-deoxy-β-D-ribo-hexopyranosyl)-β-D-mannopyranose (Compound of formula IX)

According to the method described by G. H. Veeneman and J. H. van Boom in Tetrahedron Letters (1990), 31, pp. 275–278, dissolve at −20° C. 8.53 mmol of the product of Preparation I and 7.25 mmol of 1,6:2,3-dianhydro-β-D-mannopyranose in 220 ml of toluene in the presence of a molecular sieve and 21.3 mmol of N-iodosuccinimide, then add dropwise 1.7 mmol of a 0.04M trifluoromethanesulphonic acid solution. Leave the reaction medium stirring for 2.5 hours, filter and purify on a silica column to obtain 3.07 g of 1,6:2,3-dianhydro-4-O-(2,4,6-tri-O-benzoyl-3-deoxy-β-D-ribo-hexopyranosyl)-β-D-manopyranose.

Crystallize in a mixture of ethyl acetate and hexane (90:10 V/V).

Yield: 65%
Melting point: 153° C.
$[\alpha]_D^{20} = -12°$ (C=1.10 in $CH_2Cl_2$)

Preparation IV 1,6:2,3-Dianhydro-4-O-(3-deoxy-β-D-ribo-hexopyranosyl)-β-D-mannopyranose (Compound of formula X)

Subject 1,6:2,3-dianhydro-4-O-(2,4,6-tri-O-benzoyl-3-deoxy-β-D-ribo-hexopyranosyl)-β-D-mannopyranose to a debenzoylation using sodium methanolate, to obtain 1,6:2,3-dianhydro-4-O-(3-deoxy-β-D-ribo-hexopyranosyl)-β-D-mannopyranose.

Yield: 95%
$[\alpha]_D^{20} = -46°$ (C=1.02 in $CH_3OH$)

Preparation V

3-O-Acetyl-1,6-anhydro-2-O-benzyl-4-O-(benzyl 2-O-acetyl-3-deoxy-β-D-ribo-hexopyranosyluronate)-β-D-glucopyranose (Compound of formula VI)

This compound was prepared from 1,6:2,3-dianhydro-4-O-(3-deoxy-β-D-ribo-hexopyranosyl)-β-D-mannopyranose, the compound described in Preparation IV, using processes similar to those already described by M. Petitou and C. A. A. van Boeckel in "Chemical Synthesis of heparin fragments and analogues" pp. 203–210—Progress in the Chemistry of Organic Natural Products, Ed. Springer Verlag Vienna—N.Y. (1992), and in particular: formation of 1,6:2,3-dianhydro-4-O-(3-deoxy-4,6-O-isopropylidene-β-D-ribo-hexapyranosyl)-β-D-mannopyranose, reaction with sodium benzylate, acetylation, removal of the isopropylidene radical using acetic acid, silylation, reaction with laevulinic anhydride, oxidation according to Jones' conditions, esterification using benzyl bromide and then treatment with hydrazine.

The different stages are indicated below.

STAGE A

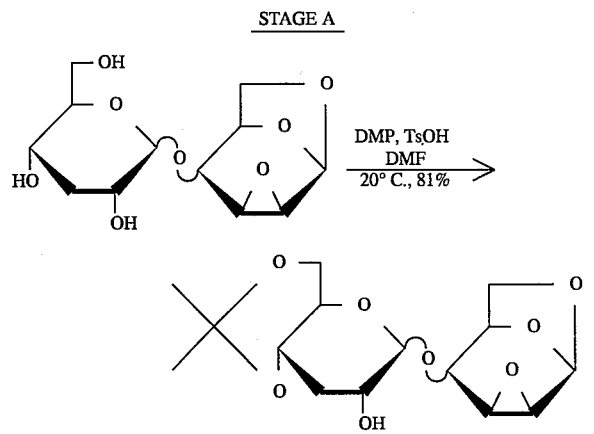

Add 1.5 mmol of p-toluenesulphonic acid (camphorsulphonic acid may also be used) and 250 mmol of 2,2-dimethoxypropane dropwise and under argon to a solution of 1,6:2,3-dianhydro-4-O-(3-deoxy-β-D-ribo-hexopyranosyl)-β-D-mannopyranose in dimethylformamide (5 mmol in 35 ml). Leave stirring for 2.5 hours, then add 1.8 mmol of triethylamine. Dilute with dichloromethane, wash with water, dry over anhydrous sodium sulphate, filter and evaporate to dryness to obtain 1,6:2,3-dianhydro-4-O-(3-deoxy-4,6-O-isopropylidene-β-D-ribo-hexopryanosyl)-β-D-mannopyranose. Use this compound in the next step without purification.

Yield: 81%

STAGE B

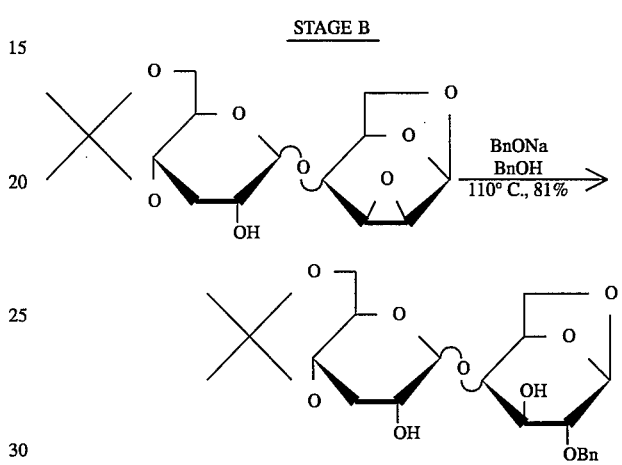

Add 25 mmol of sodium benzylate (1M solution in benzyl alcohol) to 5.0 mmol of the compound obtained in Stage A. Heat to 110° C. for 30 min. Cool, neutralize using a Dowex acid resin (AG 50 WX2), filter and remove the benzyl alcohol by evaporating under vacuum. Purify the residue on a silica column using a mixture of toluene and acetone (3:1 V/V) as eluent. The expected product is obtained in the form of a syrup.

Yield: 81%

STAGE C

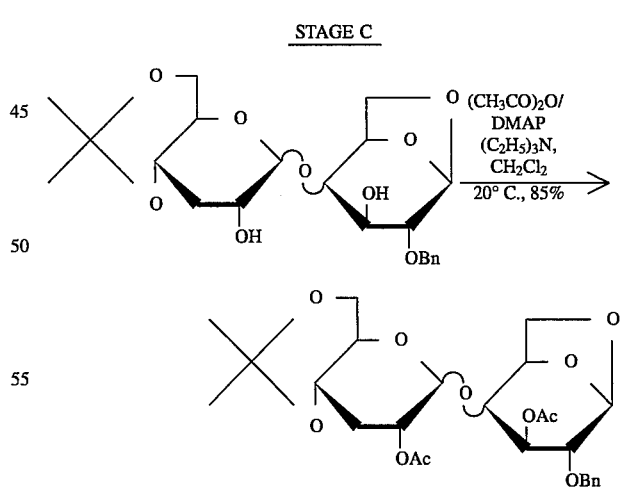

Dissolve 4.90 mmol of the compound obtained in Stage B in 22 ml of dichloromethane, cool to 0° C. and add 19.6 mmol of acetic anhydride, 1.96 mol of 4-dimethylaminopyridine and 9.81 mmol of triethylamine. Stir at room temperature for 45 min. Add methanol and keep stirring for a further 30 min. Then dilute the reaction medium with dichloromethane, wash with aqueous $KHSO_4$ solution and then with water, dry over anhydrous sodium sulphate and evaporate to dryness to obtain the expected product in the form of a syrup. Then purify on a silica column using a mixture of toluene and acetone (9:1 V/V) as eluent.

Yield: 85%

STAGE D

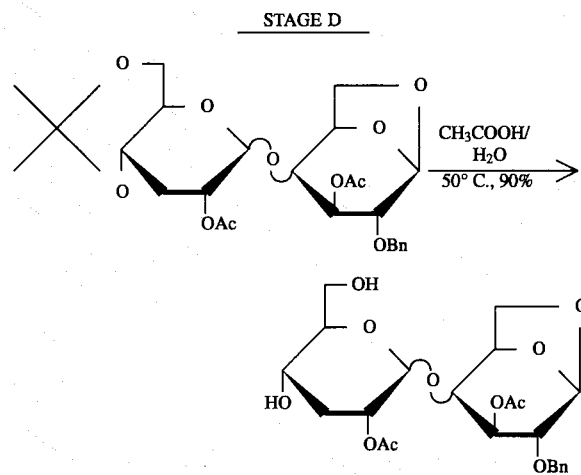

Dissolve 4.11 mmol of the compound obtained in the preceding stage in 2.2 ml of 1,1-dichloroethane and add 123 ml of aqueous acetic acid solution (70%). Leave stirring for 35 min at 50° C. Concentrate, add toluene and evaporate to obtain the expected product in the form of a syrup. Purify on a silica column using a mixture of cyclohexane and acetone (1:1 V/V) as eluent.

Yield: 90%

STAGE E

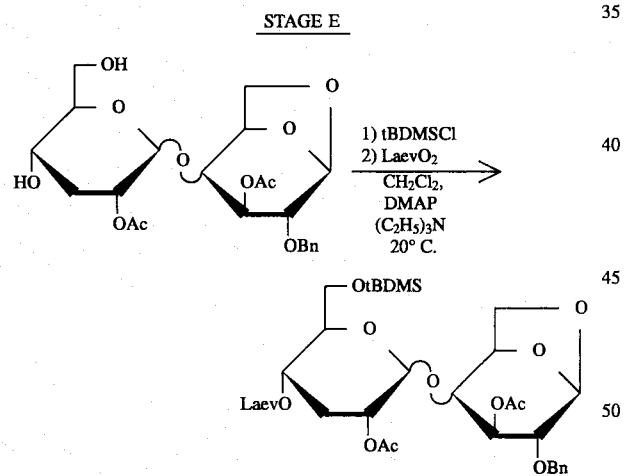

Dissolve 3.61 mmol of the compound obtained in Stage D in 3.3 ml of dichloromethane and add 1.42 mmol of 4-dimethylaminopyridine, 10.82 mmol of triethylamine and 5.41 mmol of tert-butyldimethylsilyl chloride.

Leave stirring for approximately 1 hour at 20° C., then add 43 ml of anhydrous dichloromethane and 10.8 mmol of laevulinic anhydride. Leave stirring for 2 hours, then add 150 ml of dichloromethane, wash first with aqueous $KHSO_4$ solution and then with aqueous $NaHSO_4$ solution, dry over anhydrous sodium sulphate, filter and evaporate until a brown syrup is obtained.

Use the product as it is in the next stage.

STAGE F

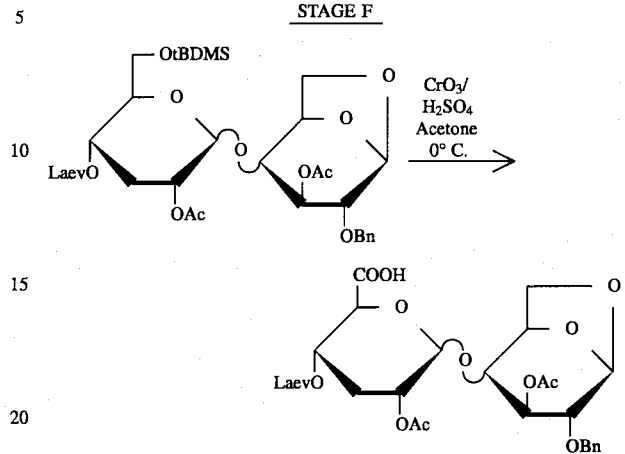

Dissolve 2.51 g of the syrup obtained in the preceding stage in 26 ml of acetone, cool to 0° C., then add 9.56 mmol of chromium trioxide and 4.2 ml of 3.5M sulphuric acid solution.

Leave stirring at room temperature for 4 hours. Then add 250 ml of dichloromethane, wash with water, dry over anhydrous sodium sulphate, filter and evaporate until a brown syrup is obtained.

Stage G

Preparation of 3-O-acetyl-1,6-anhydro-2-O-benzyl-4-O-(benzyl 2-O-acetyl-3-deoxy-4-O-laevulinyl-β-D-ribo-hexopyranosyluronate)-β-D-glucopyranose (Compound of formula XI)

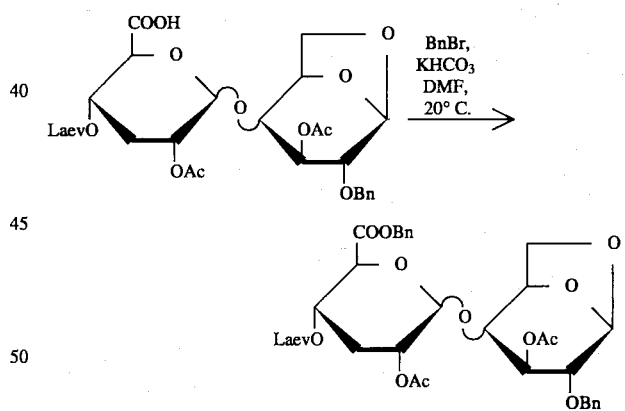

Dissolve 2.15 g of product obtained in the preceding stage in 22 ml of anhydrous dimethylformamide and add under argon 7.22 mmol of potassium bicarbonate and 10.83 mmol of benzyl bromide. Leave stirring for 3 hours, then add 0.5 ml of methanol and continue stirring for 1 hour at room temperature.

Dilute the reaction medium with ethyl acetate, wash with water, dry over anhydrous sodium sulphate, filter and evaporate until a brown syrup is obtained. Overall yield of Stages E, F, G: 81%

STAGE H

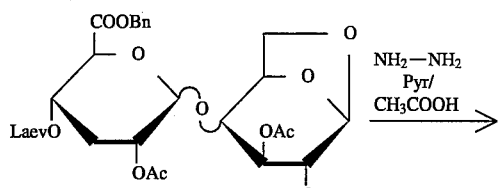

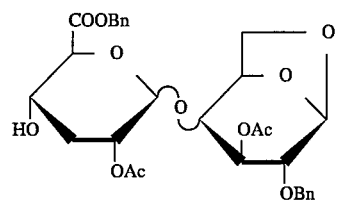

Dissolve 3.61 mmol of 3-O-acetyl-1,6-anhydro-2-O-benzyl-4-O-(benzyl 2-O-acetyl-3-deoxy-4-O-laevulinyl-β-D-ribo-hexopyranosyluronate)-β-D-glucopyranose, the compound obtained in Stage G, in 13 ml of pyridine. Cool to 0° C. and add 18.1 mmol of hydrazine [1M solution in a mixture of pyridine and acetic acid (3:2 V/V)]. Leave the reaction mixture stirring for 15 min at room temperature. Concentrate, add dichloromethane, wash with aqueous KHSO$_4$ solution, then with water and thereafter with aqueous NaHCO$_3$ solution and again with water. Dry over sodium sulphate, filter and evaporate to dryness to obtain a brown syrup. The 3-O-acetyl-1,6-anhydro-2-O-benzyl-4-O-(benzyl 2-O-acetyl-3-deoxy-β-D-ribo-hexopyranosyluronate)-β-D-glucopyranose is purified on a silica column using a mixture of cyclohexane and acetone (2:1 V/V) as solvent.

Yield: 86%

$[\alpha]_D^{20} = -78°$ (C=0.7 in CH$_2$Cl)

Preparation VI

O-(Benzyl 2-O-acetyl-3-deoxy-4-O-laevulinyl-β-D-ribo-hexopyranosyluronate)-(1→4)-3,6-di-O-acetyl-2-O-benzyl-D-glucopyranosyl)trichloroacetimidate (Compound of formula XIIa)

This compound was prepared from 3-O-acetyl-1,6-anhydro-2-O-benzyl-4-O-(benzyl 2-O-acetyl-3-deoxy-4-O-laevulinyl-β-D-ribo-hexopyranosyluronate)-β-D-glucopyranose, the compound described in Preparation V, according to known methods, and in particular acetolysis, anomeric deprotection and formation of the imidate. The different stages are given below.

STAGE A

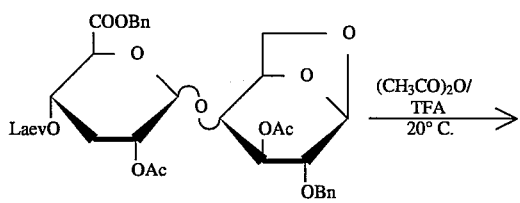

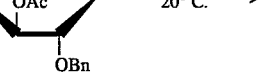

-continued
STAGE A

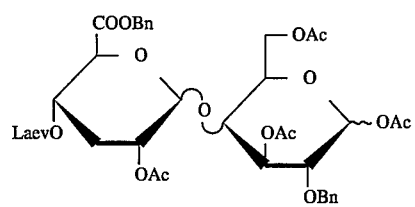

To 1.02 mmol of product obtained in Preparation V, add 102 mmol of acetic anhydride and 10.2 mmol of trifluoroacetamide. Leave the mixture stirring for 2 hours under argon. Then evaporate until a brown syrup is obtained and purify on a silica column using a mixture of cyclohexane and ethyl acetate (2:3 V/V) as eluent.

STAGE B

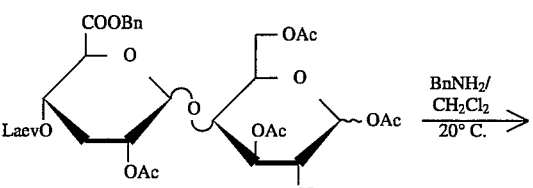

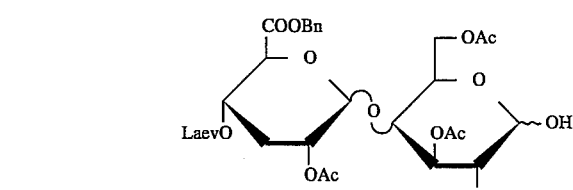

Dissolve 1.52 mmol of the compound obtained in the preceding stage in dichloromethane and add 57.9 mmol of benzylamine. Leave stirring for 4 hours at room temperature, then leave at −20° C. overnight. Add ethyl ether and wash with 1N aqueous hydrochloric acid solution. Extract with dichloromethane, dry over anhydrous sodium sulphate and evaporate until a brown syrup is obtained. Purify on a silica column using a mixture of toluene and acetone (5:1 V/V) as eluent.

STAGE C

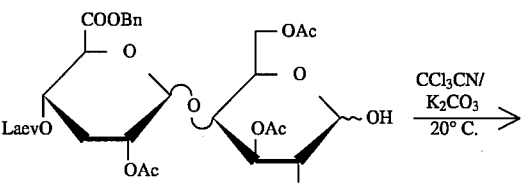

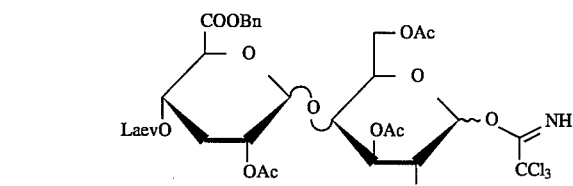

Use 0.246 mmol of the disaccharide obtained in the preceding stage, dissolved in dichloromethane. Add under argon 0.39 mmol of potassium carbonate and 1.23 mmol of trichloroacetonitrile. Leave stirring for 16 hours, filter and evaporate to dryness. O-(Benzyl 2-O-acetyl-3-deoxy-4-O-laevulinyl-β-D-ribo-hexopyranosyluronate)-(1→4)-3,6-di-O-acetyl-2-O-benzyl-D-glucopyranosyl) trichloroacetimidate is obtained in the form of a mixture of anomers.

Yield: 62% (overall)

Preparation VII 1,6:2,3-Dianhydro-4-O-(3-deoxy-α-D-ribo-hexopyranosyl)-β-D-mannopyranose (Compound of formula XV—gluco and ido mixture)

Stage A 1,6:2,3-Dianhydro-4-O-(3-deoxy-6-ido-β-D-ribo-hexopyranosyl)-β-D-mannopyranose To a solution of 1,6:2,3-dianhydro-4-O-(3-deoxy-β-D-ribo-hexopyranosyl)-β-D-mannopyranose (22.81 mmol) in 400 ml of a mixture of dichloromethane and acetonitrile, add 68.43 mmol of triphenylphosphine, 68.43 mmol of imidazole and 29.65 mmol of iodine. Leave stirring at 70° C. for 4 hours. Evaporate the solution and purify the syrup thereby obtained on a silica column using a mixture of dichloromethane and acetone (10:1 V/V) as solvent. 1,6:2, 3-Dianhydro-4-O-(3-deoxy-6-ido-β-D-ribo-hexopyranosyl)-β-D-mannopyranose is thereby obtained.

Yield: 72%

Stage B

Dissolve 23.4 mmol of 1,6:2,3-dianhydro-4-O-(3-deoxy-6-ido-β-D-ribo-hexopyranosyl)-β-D-mannopyranose in 150 ml of methanol and add 42 mmol of sodium methylate dissolved in methanol (1M). Heat the mixture for 9 hours at 80° C., cool and purify on a Sephadex LH-20 column, eluting with a mixture of dichloromethane and methanol (1:1 V/V). 1,6:2,3-Dianhydro-4-O-(3-deoxy-5,6-exomethylene-β-D-ribo-hexopyranosyl)-β-D-mannopyranose is thereby obtained. Dissolve 13.3 mmol of this compound in 100 ml of tetrahydrofuran, and add dropwise at 20° C. 54.4 mmol of diborane dissolved in tetrahydrofuran. Leave stirring for two hours, then add 65.28 mmol of ethanol. Leave stirring for one hour, then add 24 ml of 3M sodium hydroxide solution and 24 ml of 30% hydrogen peroxide solution. Heat to 50° C., neutralize on Dowex acid resin (AG 50WX4) and evaporate to dryness to obtain 1,6:2,3-dianhydro-4-O-(3-deoxy-α-D-ribo-hexopyranosyl)-β-D-mannopyranose in the form of a mixture of gluco and ido disaccharides (1:6.25).

Preparation VIII

3-O-Acetyl-1,6-anhydro-2-O-benzyl-4-O-(benzyl 2-O-acetyl-3-deoxy-4-O-laevulinyl-α-L-lyxo-hexopyranosyluronate)-β-D-glucopyranose (Compound of formula XVI)

3-O-Acetyl-1,6-anhydro-2-O-benzyl-4-O-(benzyl-2-O-acetyl-3-deoxy-4-O-laevulinyl-α-L-lyxo-hexopyranosyluronate)-β-D-glucopyranose is prepared from the compound described in Preparation VII, employing standard processes [G. Jaurand et al. (Bioorganic and Medicinal Chemistry Letters (1992), 2 (No. 9), pp. 897–900); J. Basten et al. (Bioorganic and Medicinal Chemistry Letters (1992), 2 (No. 9), pp. 901–904); J. Basten et al. (Bioorganic and Medicinal Chemistry Letters (1992), 2 (No. 9), pp. 905–910)] and in particular, formation of two corresponding 4',6'-isopropylidenes, purification and separation of the gluco and ido isomers on a silica column, reaction with sodium benzylate, acetylation, removal of the isopropylidene radical, selective silylation, reaction with laevulinic anhydride, oxidation according to Jones' conditions and esterification using benzyl bromide.

Yield 45%

The different stages are given below.

STAGE A

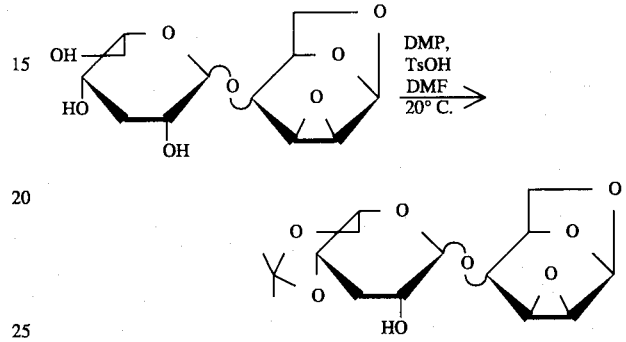

Dissolve 3.6 mmol of 1,6:2,3-dianhydro-4-O-(3-deoxy-α-D-ribo-hexopyranosyl)-β-D-mannopyranose in 25 ml of dimethylformamide and add 21.64 mmol of dimethoxypropane and 3.96 mmol of p-toluenesulphonic acid (camphorsulphonic acid may also be used). Leave stirring for 1 hour 30 min and introduce 5.94 mmol of triethylamine. Concentrate until a syrup is obtained and purify on a silica column using a mixture of toluene and ethyl acetate (2:3 V/V) as eluent.

Yield: 70%

STAGE B

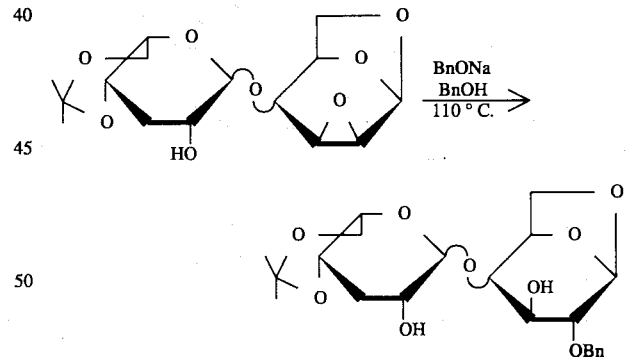

To 6.81 mmol of the compound obtained in Stage A, add 29.7 mmol of sodium benzylate dissolved in benzyl alcohol (1M). Heat at 110° C. with stirring for 1 hour. Then dilute with 200 ml of dichloromethane, thereafter neutralize using a Dowex acid resin (AG 50 WX4), filter and evaporate under vacuum to obtain a brown syrup. Purify on a silica column using a mixture of dichloromethane and acetone (10:1 V/V) as eluent.

Yield: 85%

STAGE C

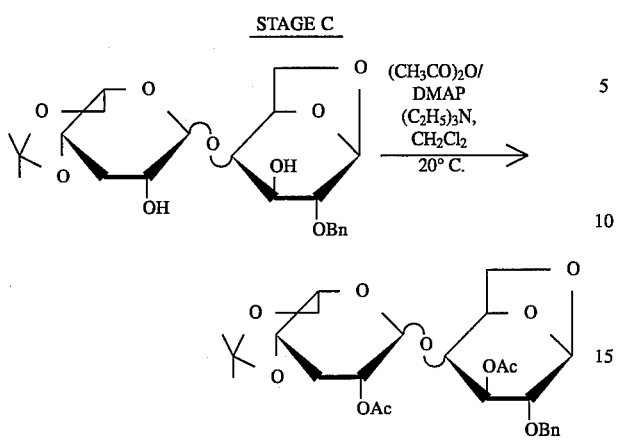

Dissolve 5.76 mmol of the compound obtained in Stage B in dichloromethane and add 3.92 mmol of 4-dimethylaminopyridine, 72.27 mmol of triethylamine and 65.7 mmol of acetic anhydride. Leave stirring at room temperature for 2 hours 30 min, then add 100 ml of dichloromethane, wash with 10% aqueous $KHSO_4$ solution, dry over anhydrous sodium sulphate, then filter.

Concentrate and purify the syrup thereby obtained on a silica column using a mixture of dichloromethane and acetone (10:1 V/V) as eluent.

$[\alpha]_D^{20} = -102°$ (C=1.37 in $CH_2Cl$)

STAGE D

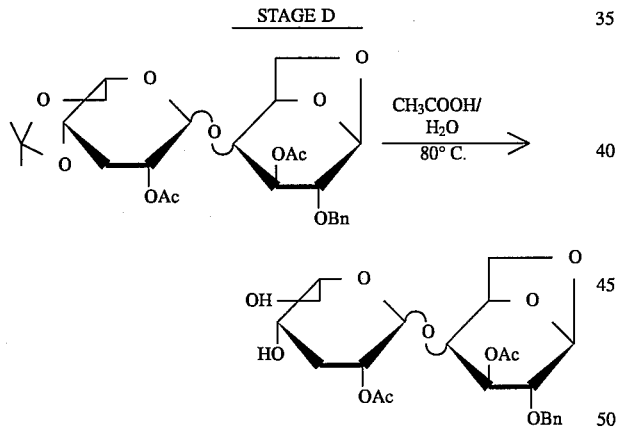

To 5.74 mmol of the compound obtained in Stage C, add 25 ml of 70% aqueous acetic acid solution. Heat at 80° C. for 6 hours. Concentrate by evaporating in the presence of toluene to obtain a yellow powder.

STAGE E

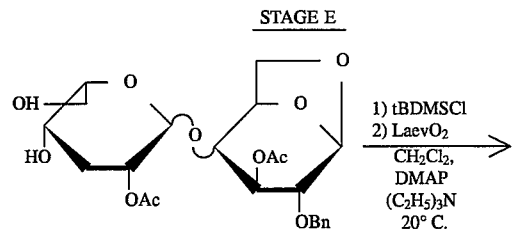

-continued
STAGE E

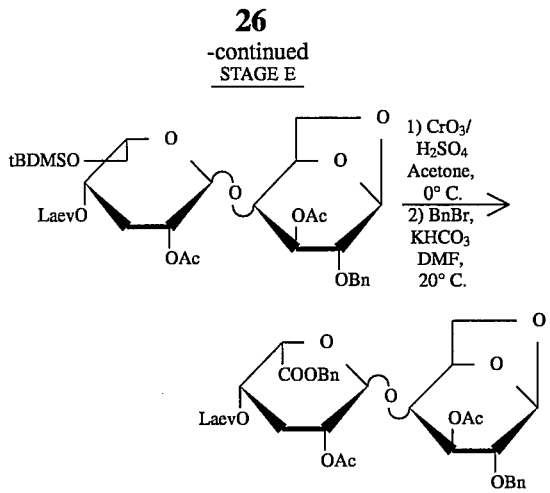

| DMAP | : 4-Dimethylaminopyridine |
|---|---|
| tBDMSCl | : tert-Butyldimethylsilyl chloride |
| BnBr | : Benzyl bromide |
| LevO2 | : Laevulinic anhydride |
| DMF | : Dimethylformamide |
| Bn | : benzyl radical |
| Ac | : acetyl radical |
| Lav | : laevulinyl radical |
| tBDMSi | : tert-butyldimethylsilyl radical |

Using the product obtained in the preceding stage, proceed as described in Preparation V, Stages E, F and G, to obtain 3-O-acetyl-1,6-anhydro-2-O-benzyl-4-O-(benzyl 2-O-acetyl-3-deoxy-4-O-laevulinyl-α-L-lyxo-hexopyranosyluronate)-β-D-glucopyranose.

Overall yield: 59%

Preparation IX

Methyl 3,6-di-O-acetyl-2-O-benzyl-4-O-(benzyl 2-O-acetyl-3-deoxy-α-L-lyxo-hexopyranosyluronate)-β-D-glucopyranoside (Compound of formula III)

Subject the disaccharide obtained in Preparation VIII to an acetolysis, treat with benzylamine, react with Vilsmeier's reagent and then with methanol in the presence of silver carbonate. Then treat the compound obtained with hydrazine to obtain methyl 3,6-di-O-acetyl-2-O-benzyl-4-O-(benzyl-2-O-acetyl-3-deoxy-α-L-lyxo-hexopyranosyluronate)-β-D-glucopyranoside. The different stages are given below:

STAGE A

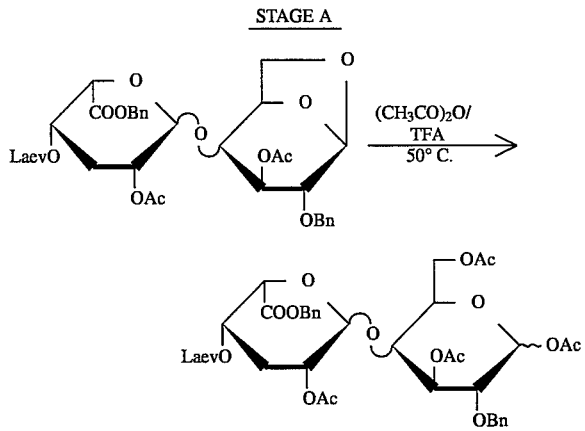

Add 102 mmol of acetic anhydride and 10.2 mmol of trifluoroacetic acid to 1.02 mmol of the disaccharide obtained in Preparation VIII, and heat at 50° C. for 2 hours under argon. Then evaporate until a brown syrup is obtained and purify as described in Preparation VI, Stage A, to obtain the expected product.
Yield: 92%

STAGE B

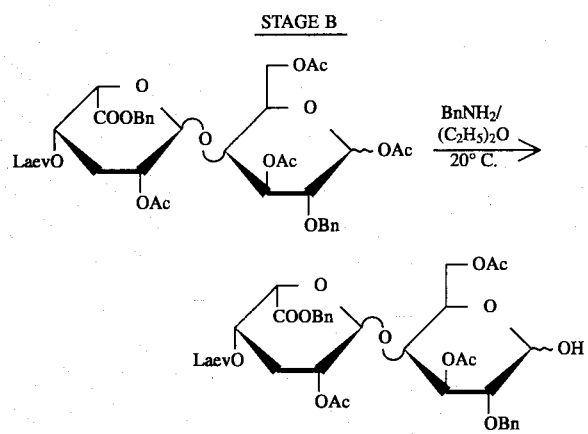

Dissolve 1.52 mmol of the compound obtained in Stage A in anhydrous ethyl ether and add 57.9 mmol of benzylamine. Proceed as described in Stage B of Preparation VI to obtain the expected product.
Yield: 79%

STAGE C

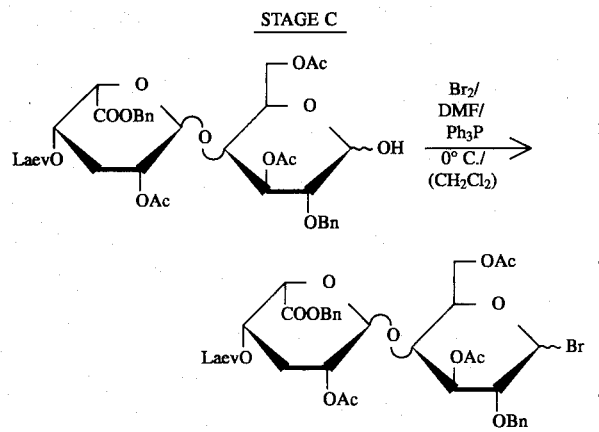

Prepare Vilsmër's reagent by mixing at 0° C. 2.15 mmol of bromine and 2.15 mmol of triphenylphosphine in 5 ml of dimethylformamide. Filter off the white precipitate under argon and add 0.269 mmol of the product obtained in Stage B, dissolved in 15 ml of anhydrous dichloromethane, while maintaining at the same temperature. Leave the reaction mixture stirring for 2 days at room temperature. Then dilute with dichloromethane, wash with water cooled to 0° C. until pH 6 is obtained, dry over anhydrous sodium sulphate and concentrate until a syrup is obtained. Purify on a silica column using a mixture of dichloro-methane and ethyl ether (5:1 V/V).

Yield: 77%

STAGE D

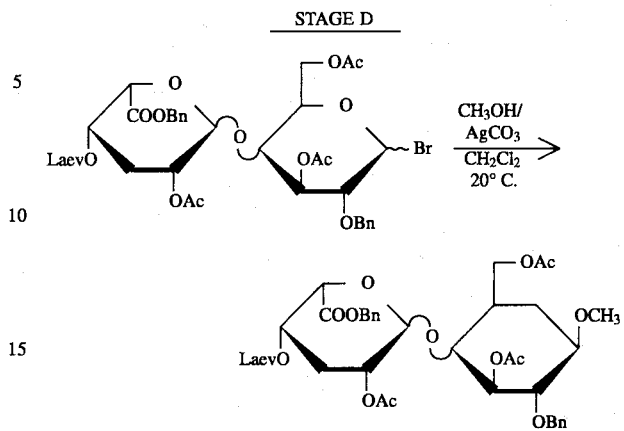

Mix 0.46 ml of methanol, 0.34 mmol of silver carbonate and 150 mg of calcium sulphate in 3 ml of dichloromethane for one hour under an argon atmosphere at 0° C. Dissolve 0.227 mmol of the compound obtained in Stage C in 8 ml of dichloromethane. Add this solution dropwise to the reaction mixture and leave stirring at 20° C. for 20 hours. Protect from light. Then dilute with dichloromethane, filter and concentrate to obtain methyl 3,6-di-O-acetyl-2-O-benzyl-4-O-(benzyl 2 -O-acetyl-3-deoxy-4-O-laevulinyl-α-L-lyxo-hexopyranosyluronate)-β -D-glucopyranoside in the form of a syrup. Purify on a silica column using a mixture of dichloromethane and ethyl ether (5:1 V/V) as eluent.
Yield: 75%
$[\alpha]_D^{20}=+27°$ (C=1.18 in $CH_2Cl_2$)

STAGE E

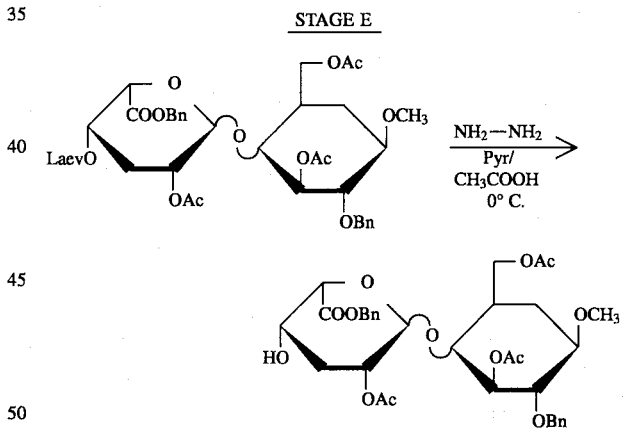

Dissolve 0.276 mmol of the product obtained in the preceding stage in 2 ml of pyridine cooled to 0° C. and add 1.38 ml of a 1M solution of hydrazine hydrate in a mixture of pyridine and acetic acid (3:2 V/V). Then concentrate the reaction mixture, add methylene chloride, wash with aqueous $KHSO_4$ solution, dry over anhydrous sodium sulphate, filter and concentrate until a syrup is obtained. Purify on a silica column using a mixture of dichloromethane and ethyl ether (3:1 V/V).
Yield: 87%
$[\alpha]_D^{20}=+10°$ (C=0.99 in $CH_2Cl_2$)

PREPARATION X

O-(2,4,6-Tri-O-benzyl-3-deoxy-α-D-ribo-hexopyranosyl)-(1→4)-O-(benzyl 2-O-acetyl-3 -deoxy-β-D-ribo-hexopyranosyluronate)-(1→4)-3-O-acetyl-1,6-anhydro-2-O-benzyl-β-D-glucopyranose (Compound of formula VII)

Dissolve 2.03 mmol of ethyl 2,4,6-tri-O-benzyl-3-deoxy-1-thio-D-ribo-hexopyranoside (Preparation II) and 1.69 mmol of 3-O-acetyl-1,6-anhydro-2-O-benzyl-4-O-(benzyl 2-O-acetyl-3 -deoxy-β-D-ribo-hexopyranosyluronate)-β-D-glucopyranose (Preparation V) in dichloromethane, and add at 20° C. some molecular sieve and then 5.07 mmol of silver trifluoromethanesulphonate and 1.52 mmol of bromine. Leave stirring for 45 minutes and then filter the reaction mixture, wash with water and evaporate to dryness.

Purify on a silica column to obtain the expected product.
Yield: 35%

PREPARATION XI

O-(6-O-Acetyl-2,4-di-O-benzyl-3-deoxy-α-D-ribo-hexopyranosyl)-(1→4)-O-(benzyl 2-O-acetyl-3 -deoxy-β-D-ribo-hexopyranosyluronate)-(1→4)-3,6-di-O-acetyl-2-O-benzyl-β-D-glucopyranosyl trichloroacetimidate (Compound of formula II)

Subject to an acetolysis 0.51 mmol of the compound obtained in Preparation X dissolved in a mixture of trifluoroacetic acid and acetic anhydride, then treat with benzylamine in ethyl ether and thereafter with trichloroacetonitrile in dichloromethane in the presence of potassium carbonate, to obtain the expected product.
Yield: 50%

EXAMPLE 1

Methyl O-(3-deoxy-2,4,6-tri-O-sulpho-α-D-ribo-hexopyranosyl)-1→4)-O-(3-deoxy-2 -O-sulpho-β-D-ribo-hexopyranosyluronate)-(1→4)-O-(2,3,6-tri-O-sulpho-α-D-glucopyranosyl)-(1→4)-O-(3 -deoxy-2-O-sulpho-α-L-lyxo-hexopyranosyluronate)-(1→4)-2,3,6-tri-O-sulpho-β-D-glucopyranoside tridecakis sodium salt

STAGE A

Methyl O-(6-O-acetyl-2,4-O-benzyl-3-deoxy-α-D-ribo-hexopyranosyl)-(1→4)-O-(benzyl 2-O-acetyl-3 -deoxy-β-D-ribo-hexopyranosyluronate)-(1→4)-O-(3,6-di-O-acetyl-2-O-benzyl-α-D-glucopyranosyl)-( 1→4)-O-(benzyl 2-O-acetyl-3-deoxy-α-L-lyxo-hexopyranosyluronate)-(1→4)-O-3,6-di-O-acetyl-2 -O-benzyl-β-D-glucopyranoside Dissolve 0.121 mmol of the compound described in Preparation XI and 0.093 mmol of the compound of Preparation IX in 3.2 ml of dichloromethane. Cool to −20° C. in the presence of molecular sieve and under an argon atmosphere, and add 0.470 ml of a solution of trimethylsilyl trifluoromethanesulphonate in dichloromethane. Leave stirring at −20° C. for 1 hour, then filter the reaction medium, wash with water, evaporate and purify on a Sephadex LH-20 column using a mixture of dichloromethane and methanol (1:1 V/V) as solvent, and then on a silica column using a mixture of cyclohexane and ethyl acetate (3:2 V/V) as solvent, to obtain the expected product.
Yield: 62%

STAGE B

Dissolve 0.052 mmol of the product obtained in the preceding stage in a mixture of dichloromethane (0.43 ml) and methanol (1.7 ml). Then add 85 mg of 10% palladium on charcoal and leave the mixture for 4 hours at 20° C. and under a slight pressure of hydrogen. Filter and evaporate to dryness to obtain methyl O-(6-O-acetyl-3-deoxy-α -D-ribo-hexopyranosyl)-(1→4)-O-(2-O-acetyl-3 -deoxy-β-D-ribo-hexopyranosyluronic acid)-(1→4)-O-(3,6-di-O-acetyl-α-D-glucopyranosyl)-(1→4)-O-(2 -O-acetyl-3-deoxy-α-L-lyxo-hexopyranosyluronic acid)-(1→4)-3,6-di-O-acetyl-β-D-glucopyranoside. Dissolve this compound in 0.96 ml of ethanol, cool to 0° C., then add 0.30 ml of 5M sodium hydroxide. Leave stirring at 0° C. for 5 hours and purify on a Sephadex G-25 column using water as eluent. Evaporate to dryness to obtain methyl O-(3-deoxy-α-D-ribo-hexopyranosyl)-(1→4)-O-(3 -deoxy-β-D-ribo-hexopyranosyluronic acid)-(1→4)-O-(α-D-glucopyranosyl)-(1→4)-O-(3-deoxy-α-L-lyxo-hexopyranosyluronic acid-(1→4)-β-D-glucopyranoside.

Dissolve this compound in 5 ml of dimethylformamide, evaporate to dryness, then dissolve again under an argon atmosphere in 2.6 ml of anhydrous dimethylformamide. Add 302 mg of sulphur trioxide/triethylamine complex and stir for 20 hours at 55° C. Cool the reaction medium, add 491 mg of sodium bicarbonate dissolved in water and leave stirring for 3 hours.

Purify on a Sephadex G-25 column using water as solvent, then lyophilize to obtain methyl O-(3-deoxy-2,4,6-tri-O-sulpho-α-D-ribo-hexopyranosyl)-(1→4)-O-(3 -deoxy-2-O-sulpho-β-D-ribo-hexopyranosyluronate)-(1→4)-O-(2,3, 6-tri-O-sulpho-α-D-glucopyranosyl)-(1→4 )-O-(3-deoxy-2-O-sulpho-α-L-lyxo-hexopyranosyluronate)-(1→4)-2,3,6-tri-O-sulpho-β-D-glucopyranoside tridecakis sodium salt.
Yield: 65%
$[\alpha]_D^{20}$=+25° (C=0.52 in $H_2O$)-Batch 1
$[\alpha]_D^{20}$=+33° (C=0.64 in $H_2O$)-Batch 2
Proton nuclear magnetic resonance spectrum: (500 MHz, solvent $D_2O$)
H1: 4.78 ppm J1–2: 7.3 Hz; H'1: 5.22 ppm, J1'–2': 1.8 Hz; H"1: 5.26 ppm, J1"–2": 3.5 Hz; H'"1: 4.78 ppm, J1'"–2'": 5.4 Hz; H"": 5.16 ppm, J1""–2"": 3.3 Hz

EXAMPLE 2

Methyl O-(3-deoxy-2,4,6-tri-O-sulpho-α-D-ribo-hexopyranosyl)-(1→4)-O-(3-deoxy-2 -O-sulpho-β-D-ribo-hexopyranosyluronate)-(1→4)-O-(2,3,6,tri-O-sulpho-α-D-glucopyranosyl)-(1→4)-O-(3 -deoxy-2-O-methyl-α-L-lyxo-hexopyranosyluronate)-(1→4)-2,3,6-tri-O-sulpho-β-D-glucopyranoside dodecakis sodium salt This compound was prepared from O-(6-O-acetyl-2,4-di-O-benzyl-3-deoxy-α-D-ribo-hexopyranosyl)-(1→4)-O-(benzyl 2-O-acetyl-3-deoxy-β-D-ribo-hexopyranosyluronate)-(1→4)-3,6-di-O-acetyl-2-O-benzyl-D-glucopyranosyl trichloroacetimidate and methyl 3,6-di-O-acetyl-2-O-benzyl-4-O-(benzyl 2-O-methyl-3 -deoxy-α-L-lyxo-hexopyranosyluronate)-β-D-glucopyranoside according to the process described in Example 1. Methyl 3,6-di-O-acetyl-2-O-benzyl-4-O-(benzyl 2-O-methyl-3 -deoxy-α-L-lyxo-hexopyranosyluronate)-β-D-glucopyranoside was prepared from 1,6:2,3-dianhydro-4-O-(3-deoxy-β-D-ribo-hexopyranosyl)-β-D-mannopyranose according to a process similar to those described in Preparations VII, VIII and IX.
$[\alpha]_D^{20}$+25° (C=0.48 in $H_2O$)
Proton nuclear magnetic resonance spectrum; (500 MHz, solvent $D_2O$)
H1: 4.82 ppm J1–2: 4.2 Hz; H'1: 5.08 ppm, J1'–2': 1.0 Hz; H"1: 5.27 ppm, J1"–2": 3.7 Hz; H'"1: 4.76 ppm, J1'"–2'": 7.7 Hz; H"": 5.15 ppm, J1""–2"": 3.5 Hz

EXAMPLE 3

Methyl O-(3-deoxy-2,4-di-O-methyl-6-O-sulpho-α-D-ribo-hexopyranosyl)-(1→4)-O-(3-deoxy-2 -O-sulpho-β-D-ribo-hexopyranosyluronate)-(1→4)-O-(2,3,6-tri-O-sulpho-α-D-glucopyranosyl)-1→4)-O-(3 -deoxy-2-O-sulpho-α-L-lyxo-hexopyranosyluronate)-(1→4)-2,3,6-tri-O-sulpho-β-D-glucopyranoside undecakis sodium salt This compound was prepared from O-(6-O-benzyl-2,4-di-O-methyl-3-deoxy-α-D-ribo-hexopyranosyl)-(1→4)-O-(benzyl 2-O-acetyl-3-deoxy-β-D-ribo-hexopyranosyluronate)-(1→4)-3,6-di-O-acetyl-2-O-benzyl-D-glucopyranosyl trichloroacetamidate and methyl 3, 6-di-O-acetyl-2-O-benzyl-4-O-(benzyl 2-O-acetyl-3-deoxy-α-L-lyxo-hexopyranosyluronate)-β -D-glucopyranoside according to the process described in Example 1. O-(6-O-Benzyl-2,4-di-O-methyl-3-deoxy-α-D-ribo-hexopyrano-syl)-(1→ 4)-O-(benzyl 2-O-acetyl-3-deoxy-β-D-ribo-hexopyranosyluronate)-(1→4)-3,6-di-O-acetyl-2 -O-benzyl-D-glucopyranosyl trichloroacetimidate was prepared from ethyl 6-O-benzyl-2,4-di-O-methyl-3-deoxy-1-thio-β-D-ribo-hexopyranoside and 3-O-acetyl-1,6-anhydro-2-O-benzyl-4-O-(benzyl 2-O-acetyl-3 -deoxy-β-D-ribo-hexopyranosyluronate)-β-D-glucopyranose according to the process described in Preparation X.

$[\alpha]_D^{20}$=+24° (C=0.6 in $H_2O$)

Proton nuclear magnetic resonance spectrum; (500 MHz, solvent $D_2O$)

H1: 4.77 ppm J1–2: 5.0 Hz; H'1: 5.22 ppm, J1'–2': 2.2 Hz; H" 1: 5.24 ppm, J1"–2": 3.7 Hz; H'''1: 4.76 ppm, J1'''–2''': 7.5 Hz; H''''':5.10 ppm, J1''''–2'''': 3.6 Hz

EXAMPLE 4

Methyl O-(3-deoxy-4-O-methyl-2,6-di-O-sulpho-α-D-ribo-hexopyranosyl)-(1→4)-O-(3-deoxy-2 -O-sulpho-β-D-ribo-hexopyranosyluronate)-(1→4)-O-(2,3,6-tri-O-sulpho-α-D-glucopyranosyl)-(1→4)-O-(3 -deoxy-2-O-sulpho-α-L-lyxo-hexopyranosyluronate)-(1→4)-2,3,6-tri-O-sulpho-β-D-glucopyranoside dodecakis sodium salt This compound was prepared according to the process described in Example 1, from the compound described in Preparation IX and O-(2,6-di-O-benzyl-4-O-methyl-3-deoxy-α-D-ribo-hexopyranosyl)-(1→4)-O-(benzyl 2-O-acetyl-3-deoxy-β-D-ribo-hexopyranosyluronate)-(1→4)-3, 6-di-O-acetyl-2-O-benzyl-D-glucopyranosyl trichloroacetimidate. The latter trisaccharide derivative was prepared from ethyl 2,6-di-O-benzyl-4-O-methyl-3-deoxy-1-thio-D-ribo-hexopyranoside and the compound described in Preparation V according to the process described in Preparations X and XI.

$[\alpha]_D^{20}$+22° (C=0.54 in $H_2O$)

Proton nuclear magnetic resonance spectrum; (500 MHz, solvent $D_2O$)

H1: 4.78 ppm J1–2: 5.1 Hz; H'1: 5.22 ppm, J1'–2': 2.6 Hz; H" 1: 5.27 ppm, J1"–2": 3.9 Hz; H'''1: 4.75 ppm, J1'''–2''': 7.9 Hz; H''''': 5.11 ppm, J1''''–2'''': 3.5 Hz

EXAMPLE 5

Methyl O-(3-deoxy-2,4,6-tri-O-sulpho-α-D-ribo-hexopyranosyl)-(1→4)-O-(3-deoxy-2 -O-methyl-β-D-ribo-hexopyranosyluronate)-(1→4)-O-( 2,3,6-tri-O-sulpho-α-D-glucopyranosyl)-(1→4)-O-(3-deoxy-2-O-methyl-α-L-lyxo-hexopyranosyluronate)-(1→4)-2,3,6-tri-O-sulpho-β-D-glucopyranoside undecakis sodium salt This compound was prepared from methyl 3,6-di-O-acetyl-2-O-benzyl-4-O-(benzyl 2-O-methyl-3 -deoxy-α-L-lyxo-hexopyranosyluronate)-β-D-glucopyranoside and O-(6-O-acetyl-2,4-di-O-benzyl-3-deoxy-α-D-ribo-hexopyranosyl)-(1→4)-O-(benzyl 2-O-methyl-3-deoxy-β-D-ribo-hexopyranosyluronate)-(1→4)-3,6-di-O-acetyl-2 -O-acetyl-2-O-benzyl-D-glucopyranosyl trichloroacetimidate according to the process described in Example 1. The trisaccharide used as starting material was prepared from 3-O-acetyl-1,6-anhydro-2-O-benzyl-4-O-(benzyl 2-O-methyl-3 -deoxy-β-D-ribo-hexopyranosyluronate)-β-D-glucopyranose and the compound described in Preparation II according to the process described in Preparations X and XI.

$[\alpha]_D^{20}$=+20° (C=0.39 in $H_2O$)

Proton nuclear magnetic resonance spectrum; (500 MHz, solvent $D_2O$)

H1: 4.83 ppm J1–2: 3.0 Hz; H'1: 5.11 ppm, J1'–2': 2.0 Hz; H" 1: 5.31 ppm, J1"–2": 3.3 Hz; H'''1: 4.68 ppm, J1'''–2''': 7.7 Hz; H''''': 5.18 ppm, J1''''–2'''': 3.2 Hz

EXAMPLE 6

Methyl O-(3-deoxy-2,4,6-tri-O-sulpho-α-D-ribo-hexopyranosyl)-(1→4)-O-(3-deoxy-2 -O-methyl-β-D-ribo-hexopyranosyluronate)-(1→4)-O-(2,3,6-tri-O-sulpho-α-D-glucopyranosyl)-(1→4 )-O-(3-deoxy-2-O-sulpho-α-L-lyxo-hexopyranosyl-uronate)-(1→4)-2,3,6 -tri-O-sulpho-β-D-glucopyranoside dodecakis sodium salt This compound was prepared according to the process described in Example 1, from O-(6-O-acetyl-2,4-di-O-benzyl-3-deoxy-α-D-ribo-hexopyranosyl)-(1→4 )-O-benzyl 2-O-methyl-3-deoxy-β-D-ribo-hexopyranosyluronate)-(1→ 4)-3,6-di-O-acetyl-2 -O-benzyl-D-glucopyranosyl trichloroacetimidate and the compound described in Preparation IX.

$[\alpha]_D^{20}$=+30° (C=0.40 in $H_2O$)

Proton nuclear magnetic resonance spectrum; (500 MHz, solvent $D_2O$)

H1: 4.77 ppm J1–2: 5.0 Hz; H'1: 5.20 ppm, J1'–2': 2.5 Hz; H"1: 5.27 ppm, J1"–2": 4.0 Hz; H'''1: 4.67 ppm, J1'''–2''': 8.0 Hz; H''''': 5.14 ppm, J1''''–2'''': 3.5 Hz

EXAMPLE 7

Methyl O-(3-deoxy-2,4,6-tri-O-sulpho-α-D-ribo-hexopyranosyl)-(1→4)-O-(3-deoxy-2 -O-methyl-β-D-ribo-hexopyranosyluronate)-(1→4)-O-(2,3,6-tri-O-sulpho-α-D-glucopyranosyl)-(1→4)-O-(3 -O-methyl-2-O-sulpho-α-L-ido-pyranosyluronate)-(1→4)-2,3,6-tri-O-sulpho-α-D-glucopyranoside dodecakis sodium salt This compound was prepared according to the process described in Example 1, from O-(6-O-acetyl-2,4-di-O-benzyl-3-deoxy-α-D-ribo-hexopyranosyl)-(1→4 )-O-benzyl 2-O-methyl-3-deoxy-β-D-ribo-hexopyranosyluronate)-(1→

4)-3,6-di-O-acetyl-2-O-benzyl-D-glucopyranosyl trichloroacetimidate and methyl 2,3,6-tri-O-benzyl-4-O-(benzyl 2-O-benzyl-3-O-methyl-α-L-idopyranosyluronate)-α-D-glucopyranoside. The latter compound was prepared according to the method described by M. Petitou and C. A. A. van Boeckel in "Chemical synthesis of heparin fragments and analogues" pp. 203–210 —Progress in the Chemistry of Organic Natural Products, Ed. Springer Verlag Vienna—N.Y. 1992.

$[\alpha]_D^{20} = +46°$ (C=0.58 in $H_2O$)

Proton nuclear magnetic resonance spectrum; (500 MHz, solvent $D_2O$)

H1: 5.10 ppm J1–2: 3.0 Hz; H'1: 5.10 ppm, J1'–2': 5.0 Hz; H"1: 5.48 ppm, J1"–2": 3.60 Hz; H'''1: 4.68 ppm, J1'''–2''': 7.5 Hz; H'''': 5.16 ppm, J1''''–2'''': 3.6 Hz

EXAMPLE 8

Methyl O-(3-deoxy-2,4-di-O-sulpho-β-D-ribo-hexopyranosyluronate)-(1→4)-O-(2,3,6-tri-O-sulpho-α-D-glucopyranosyl)-(1→4)-O-(3-deoxy-2-O-sulpho-β-D-ribohexopyranosyluronate)-(1→4)-O-(2,3,6-tri-O-sulpho-α-D-glucopyranosyl)-(1→4)-O-(3-deoxy-2-O-sulpho-α-L-lyxo-hexopyranosyluronate)-(1→4)-2,3,6-tri-O-sulpho-β-D-glucopyranoside hexadecakis sodium salt This compound was prepared from O-(benzyl 2-O-acetyl-3-deoxy-4-O-laevulinyl-β-D-ribo-hexopyranosyluronate)-(1→4)-3,6-di-O-acetyl-2-O-benzyl-D-glucopyranosyl trichloroacetimidate (Preparation VI) and 3-O-acetyl-1,6-anhydro-2-O-benzyl-4-O-(benzyl 2-O-acetyl-3-deoxy-β-D-ribo-hexopyranosyluronate)-β-D-glucopyranose (Preparation V). By reacting these two compounds under the conditions described in Example 1, Stage A, the following compound is obtained:

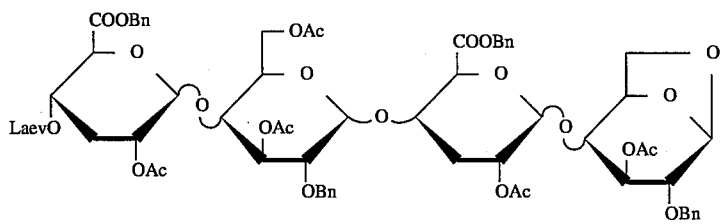

Yield: 64%

The product thereby obtained is subjected to an acetolysis according to the process described in Preparation VI, Stage A, and then to the action of benzylamine under the conditions described in Stage B of Preparation VI to liberate the anomeric hydroxyl. The corresponding imidate is then obtained by reaction with trichloroacetonitrile in the presence of potassium carbonate according to the process described in Preparation VI, Stage C.

By reacting the latter product with methyl 3,6-di-O-acetyl-2-O-benzyl-4-O-(benzyl 2-O-acetyl-3-deoxy-α-L-lyxo-hexopyranosyluronate)-β-D-glucopyranoside (Preparation IX), methyl O-(3-deoxy-2,4-di-O-sulpho-β-D-ribo-hexopyranosyluronate)-(1→4)-O-(2,3,6-tri-O-sulpho-α-D-glucopyranosyl)-(1→4)-O-(3-deoxy)-2-O-sulpho-β-D-ribo-hexopyranosyluronate)-(1→4)-O-(2,3,6-tri-O-sulpho-α-D-glucopyranosyl)-(1→4)-O-(3-deoxy-2-O-sulpho-α-L-lyxo-hexopyranosyluronate)-(1→4)-2,3,6-tri-O-sulpho-β-D-glucopyranoside, hexadecakis sodium salt.

Proton nuclear magnetic resonance spectrum; (500 MHz, solvent $D_2O$)

H1: 4.78 ppm J1–2: 7.0 Hz; H'1: 5.22 ppm, J1'–2': 1.9 Hz; H"1: 5.25 ppm, J1"–2": 3.50 Hz; H'''1: 4.79 ppm, J1'''–2''': 5.6 Hz; H'''': 5.31 ppm, J1–2: 3.50 Hz; H''''': 4.80 ppm, J1'''''–2''''': 5.9 Hz

We claim:

1. A compound having the formula

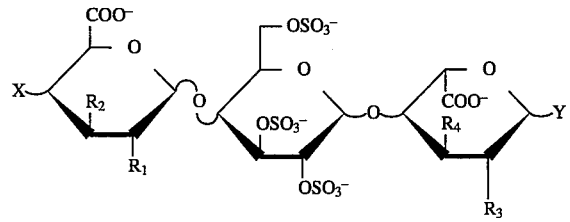

in which X is selected from the group consisting of —$OSO_3^-$, a radical of formula A, $$R—O \qquad (A),$$

a radical of formula B,

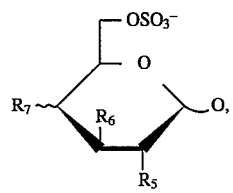

(B)

and a radical of formula C,

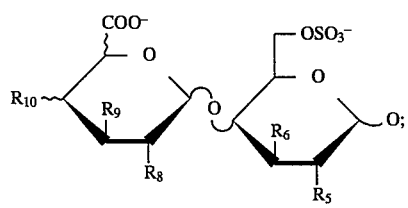

(C)

Y represents a radical of formula D,

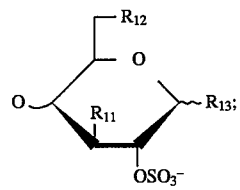

(D)

R is selected from the group consisting of linear $(C_1-C_6)$alkyl and branched $(C_3-C_6)$alkyl;

$R_1$, $R_3$, $R_5$, $R_7$, $R_8$, $R_{10}$, $R_{12}$ and $R_{13}$, which may be identical to or different from each other, are each selected from the group consisting of hydroxyl, linear $(C_1-C_6)$alkoxy, branched $(C_3-C_6)$alkoxy and $-OSO_3^-$;

$R_2$, $R_4$, $R_6$, $R_9$ and $R_{11}$, which may be identical to or different from each other, are each selected from the group consisting of hydrogen, hydroxyl, linear $(C_1-C_6)$alkoxy, branched $(C_3-C_6)$alkoxy and $-OSO_3^-$;

with the proviso that at least one of $R_2$, $R_4$, $R_6$, $R_9$ and $R_{11}$ is hydrogen;

or a pharmaceutically acceptable salt or acid thereof.

2. A compound according to claim 1, having the formula:

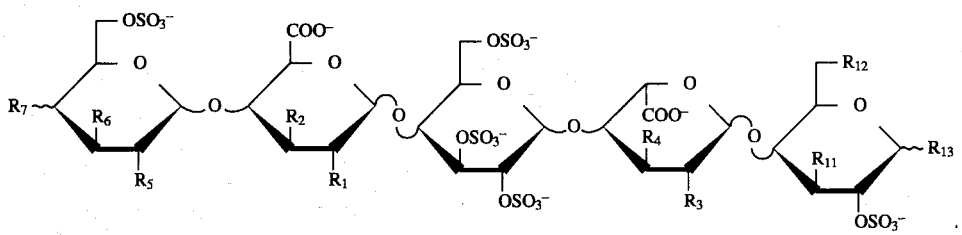

3. A compound according to claim 1, having the formula:

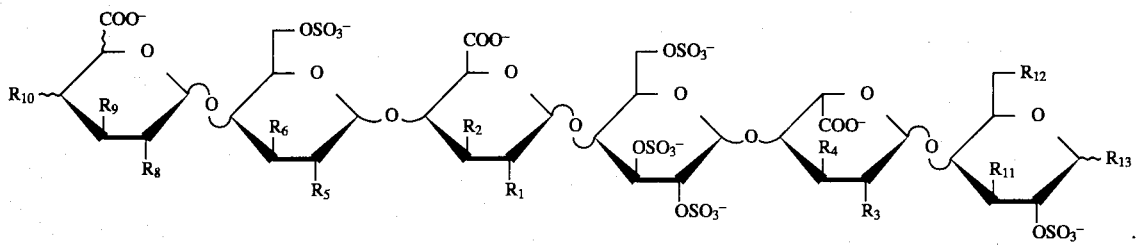

4. A compound according to claim 1, in which $R_1$, $R_3$, $R_5$, $R_7$, $R_8$, $R_{10}$ and $R_{13}$ which may be identical to or different from each other, are each selected from the group consisting of linear $(C_1-C_6)$alkoxy, branched $(C_3-C_6)$alkoxy and $-OSO_3-$;

$R_2$, $R_4$, $R_6$ and $R_9$, which may be identical to or different from each other, are each selected from the group consisting of hydrogen, linear $(C_1-C_6)$alkoxy, branched $(C_3-C_6)$alkoxy and $-OSO_3-$;

$R_{11}$ is selected from the group consisting of hydrogen, linear $(C_1-C_6)$alkoxy, branched $(C_3-C_6)$alkoxy and $-OSO_3^-$;

with the proviso that at least one of $R_2$, $R_4$, $R_6$, $R_9$ and $R_{11}$ is hydrogen;

and $R_{12}$ is selected from the group consisting of hydroxyl and $-OSO_3^-$.

5. A compound according to claim 1, in which $R_2$ represents hydrogen.

6. A compound according to claim 1, in which $R_2$ and $R_6$ represent hydrogen;

$R_3$, $R_{11}$ and $R_{12}$ represent $-OSO_3^-$;

and $R_{13}$ is selected from the group consisting of linear $(C_1-C_6)$alkoxy, branched $(C_3-C_6)$alkoxy and $-OSO_3^-$.

7. A compound according to claim 1, selected from the group consisting of methyl O-(3-deoxy-2,4,6-tri-O-sulpho-α -D-ribo-hexopyranoxyl)-(1→4)-O-(3-deoxy-2-O-sulpho-β-D-ribo-hexopyranosyluronate)-(1→4)-O-(2,3,6-tri-O-sulpho-α -D-glucopyranosyl)-(1→4)-O-(3 -deoxy-2-O-sulpho-α-L-lyxo-hexopyranosyluronate)-(1→4)-2,3,6-tri-O-sulpho-β-D-glucopyranoside, and its pharmaceutically acceptable salts.

8. A compound according to claim 1, selected from the group consisting of methyl O-(3-deoxy-2,4,-di-O-methyl-6-O-sulpho-α -D-ribo-hexopyranoxyl)-(1→4)-O-(3 -deoxy-2-O-sulpho-β-ribo-hexopyranosyluronate)-(1→4)-O-(2,3,6-tri-O-sulpho-α-D-glucopyranosyl)-(1→4 )-O-(3-deoxy-2-O-sulpho-α-L-lyxo-hexopyranosyluronate)-(1→4)-2,3,6-tri-O-sulpho-β-D-glucopyranoside, and its pharmaceutically acceptable salts.

9. A compound according to claim 1, selected from the group consisting of methyl O-(3-deoxy-4-O-methyl-2,6-di-O-sulpho-α-D-ribo-hexopyranosyl)-(1→4)-O-(3 -deoxy-2-O-sulpho-β-ribo-hexopyranosyluronate)-(1→4)-O-(2,3,6-tri-O-sulpho-α-D-glucopyranosyl)-(1→4 )-O-(3-deoxy-2-O-sulpho-α-D-lyxo hexopyranosyluronate)-(1→4)-2,3,6-tri-O-sulpho-β-D-glucopyranoside, and its pharmaceutically acceptable salts.

10. A pharmaceutical composition comprising a pharmaceutically effect amount of the compound of claim 1 or a pharmaceutically acceptable salt or acid thereof in combination with a pharmaceutically acceptable, non-toxic, inert excipient.

11. 1,6:2,3-Dianhydro-4-O-(2,4,6-tri-O-benzoyl-3-deoxy-β-D-ribo-hexopyranosyl)-β-D-mannopyranose, the compound of formula IX:

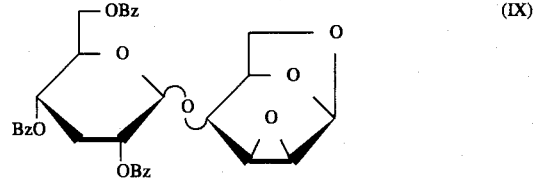

(IX)

in which Bz represents benzyol.

12. 1,6:2,3-Dianhydro-4-O-(3-deoxy-β-D-ribo-hexopyranosyl)-β-D-mannopyranose, the compound of formula X:

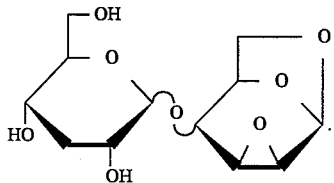 (X)

13. A compound of formula XI:

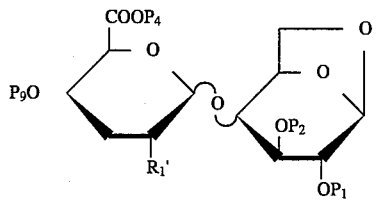 (XI)

in which $R_1'$ is selected from the group consisting of linear ($C_1$–$C_6$)alkoxy, branched ($C_1$–$C_6$)alkoxy, an acyclic acyloxy radical having 1 to 6 carbon atoms, an aromatic acyloxy radical, and a 2-alkenyloxy radical having 2 to 7 carbon atoms;

$P_1$ and $_2$, which may be identical to or different from each other, each represent a protective group selected from the group consisting of an acyclic acyl radical having 1 to 6 carbon atoms, an aromatic acyl radical, a 2-alkenyl radical having 2 to 7 carbon atoms, and benzyl;

$P_4$ is an alkyl radical having 1 to 6 carbon atoms or benzyl; and $P_9$ is selected from the group consisting of a laevulinyl radical and a chloroacetyl radical.

\* \* \* \* \*